US010975160B2

(12) United States Patent
Moon et al.

(10) Patent No.: US 10,975,160 B2

(45) Date of Patent: Apr. 13, 2021

(54) ANTIBODY BINDING TO CARBONIC ANHYDRASE AND USE THEREOF

(71) Applicant: Aprogen KIC Inc., Seongnam-si (KR)

(72) Inventors: Yoo Ri Moon, Seoul (KR); Gil Yong Ji, Seoul (KR)

(73) Assignee: APROGEN KIC INC., Seongnam-si (KR)

( * ) Notice: Subject to any disclaimer, the term of this patent is extended or adjusted under 35 U.S.C. 154(b) by 211 days.

(21) Appl. No.: 16/263,349

(22) Filed: Jan. 31, 2019

(65) Prior Publication Data

US 2019/0153116 A1 May 23, 2019

Related U.S. Application Data

(60) Division of application No. 15/344,764, filed on Nov. 7, 2016, now Pat. No. 10,246,517, which is a continuation-in-part of application No. PCT/KR2016/005722, filed on May 30, 2016.

(51) Int. Cl.

| | |
|---|---|
| ***G01N 33/574*** | (2006.01) |
| ***C07K 16/30*** | (2006.01) |
| ***A61K 47/68*** | (2017.01) |
| ***A61K 45/06*** | (2006.01) |
| ***A61K 33/24*** | (2019.01) |
| ***C07K 16/40*** | (2006.01) |
| *A61K 39/00* | (2006.01) |

(52) U.S. Cl.

CPC .......... *C07K 16/3015* (2013.01); *A61K 33/24* (2013.01); *A61K 45/06* (2013.01); *A61K 47/6803* (2017.08); *A61K 47/6855* (2017.08); *A61K 47/6871* (2017.08); *C07K 16/30* (2013.01); *C07K 16/3023* (2013.01); *C07K 16/40* (2013.01); *G01N 33/57415* (2013.01); *G01N 33/57484* (2013.01); *A61K 2039/505* (2013.01); *C07K 2317/14* (2013.01); *C07K 2317/24* (2013.01); *C07K 2317/34* (2013.01); *C07K 2317/41* (2013.01); *C07K 2317/56* (2013.01); *C07K 2317/565* (2013.01); *C07K 2317/73* (2013.01); *C07K 2317/732* (2013.01); *C07K 2317/734* (2013.01); *C07K 2317/90* (2013.01); *G01N 2333/988* (2013.01)

(58) Field of Classification Search

CPC ............ A61K 47/6803; A61K 47/6855; A61K 47/6871; C07K 16/30; C07K 2317/56; C07K 2317/565

See application file for complete search history.

(56) References Cited

U.S. PATENT DOCUMENTS

2013/0231465 A1 9/2013 Zeidler

FOREIGN PATENT DOCUMENTS

WO 2011-139375 11/2011

OTHER PUBLICATIONS

Kristiina Nordfors, et al., "Research article the tumour-associated carbonic anhydrases CA II, CA IX and CA XII in a group of medulloblastomas and supratentorial primitive neuroectodermal tumours: an association of CA IX with poor prognosis", BMC Cancer Apr. 18, 2010, 10:148, London, United Kingdom.

Barbara Ulmasov, et al., "Purification and kinetic analysis of recombinant CA XII, a membrane carbonic anhydrase overexpressed in certain cancers", PNAS (Proceedings of the National Academy of Sciences of the United States of America) Dec. 19, 2000, vol. 97, No. 26, pp. 14212-14217.

Narges K. Tafreshi et al., "Carbonic Anhydrase IX as an Imaging and Therapeutic Target for Tumors and Metastases", Subcellular Biochemistry, vol. 75, Chapter 12, pp. 221-254, Sep. 17, 2013.

J Závada, et al., "Human tumour-associated cell adhesion protein MN/CA IX: identification of M75 epitope and of the region mediating cell adhesion", British Journal of Cancer, vol. 82, No. 11, pp. 1808-1813, Jun. 2000.

Dovile Dekaminaviciute et al., "Development and Characterization of New Monoclonal Antibodies against Human Recombinant CA XII", BioMed Research International, vol. 2014, May 20, 2014, Article ID.309307.

Korean Intellectual Property Office, International Search Report and Written Opinion of Application No. PCT/KR2016/005722, dated Feb. 15, 2017.

NCBI Reference Sequence: NP_001209.1, Definition carbonic anhydrase 12 isoform 1 precursor [*Homo sapiens*], Accession NP_001209 NP_060159, Version NP_001209.1, DBSOURCE REFSEQ: accession NM_001218.4.

*Primary Examiner* — Lei Yao

(74) *Attorney, Agent, or Firm* — Lex IP Meister, PLLC

(57) ABSTRACT

Provided is an antibody that recognizes and binds to carbonic anhydrase or antigen-binding fragment, a nucleic acid molecule coding for the antibody or antigen-binding fragment, a vector carrying the nucleic acid molecule, a host cell including the nucleic acid molecule or the vector, and use of the antibody or antigen-binding fragment thereof in the alleviation, prevention, treatment or diagnosis of solid cancers.

15 Claims, 27 Drawing Sheets

Specification includes a Sequence Listing.

[Fig. 1]
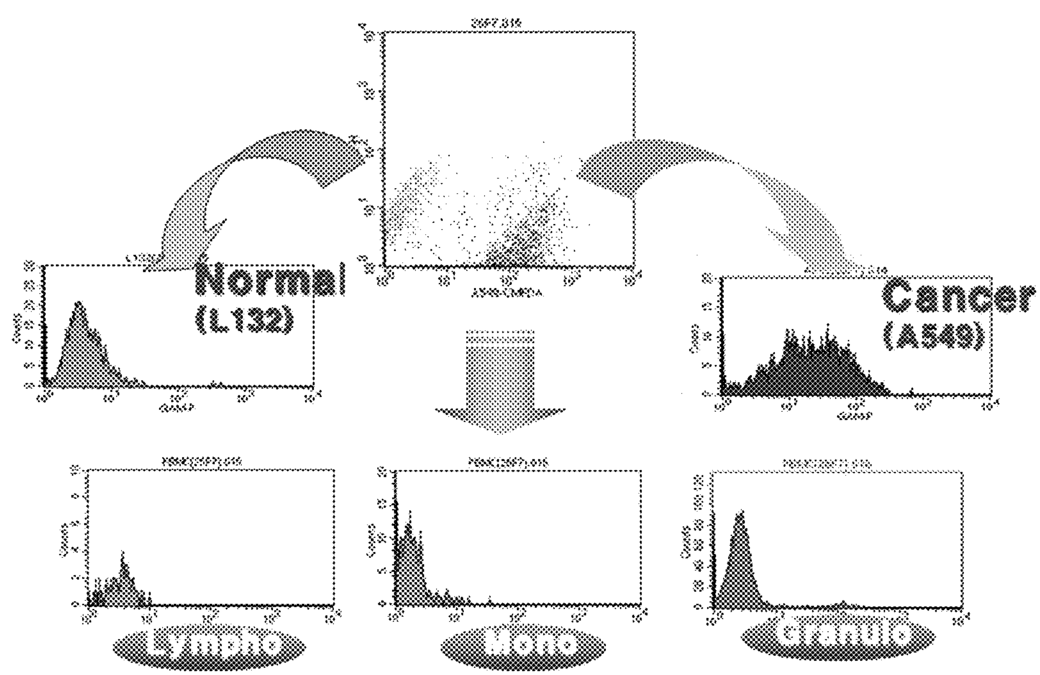

[Fig. 2]

| **27B6 Ab** | $V_H$ | QVQLQQSGPQLVWPGASVKISCNTSGYSFTNYWIHWVKQRPGQGLEWIGMIDPSDSETRLNQKFKDKTTLTVDRSSSTAYMQVSSSTSEDSAVYYCTRGIRGGYYAMDYWGQGTSVTVSS | CDR1: GYSFTNYW<br>CDR2: IDPSDSET<br>CDR3: TRGIRGGYYAMDY |
|---|---|---|---|
| | $V_L$ | DIQMTQTTSSLSASLGDRVTISCRASQDISNYLNWYQQKPEGTVKLLIYYTSRLHSGVPSRFSGSGSGTDYSLTISNLEQEDIATYFCQQGDTLPRTFGEGTKLEIR | CDR1: QDISNY<br>CDR2: YTS<br>CDR3: QQGDTLPRT |
| 4B4 Ab | $V_H$ | EIQLQQSGPELVKPGASVKISCKASGYSYTDYNIYWVRQSQGKSLDWIGYIDPANGDTTYNQKFKGKATLTVDKSSSTAFMHLNSLTSDGSAVYFCARPIYYGVYWYFDVWGAGTTVTVS | CDR1: GYSYTDYN<br>CDR2: IDPANGDT<br>CDR3: ARPIYYGVYWYFDV |
| | $V_L$ | DIVMTQAAPSVPVTPGESVSISCRSSKSLLHSNGNTYLYWFLQRPGQSPQLLIYRMSNLASGVPDRFSGSGSGTAFTLRISRVEAEDVGVYYCMQHLEYPFTFGSGTKLEIK | CDR1: KSLLHSNGNTY,<br>CDR2: RMS<br>CDR3: MQHLEYPFT |

[Fig. 3]
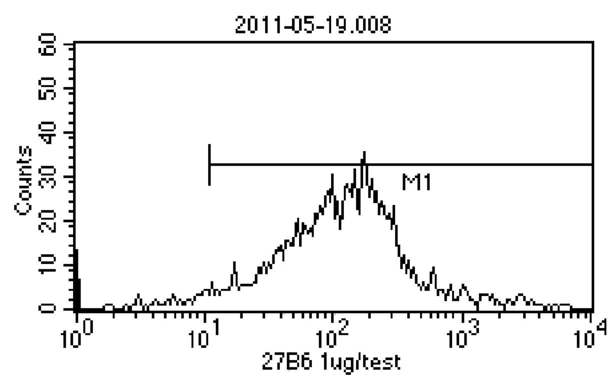
| Marker | % Gated | Mean |
|---|---|---|
| All | 100.00 | 195.55 |
| M1 | 97.70 | 200.00 |
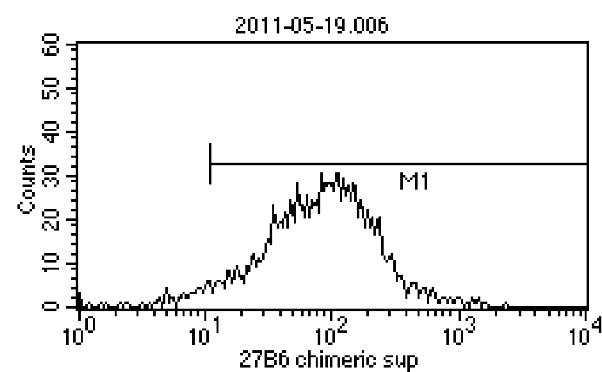
| Marker | % Gated | Mean |
|---|---|---|
| All | 100.00 | 111.58 |
| M1 | 97.20 | 114.57 |

[Fig. 4]
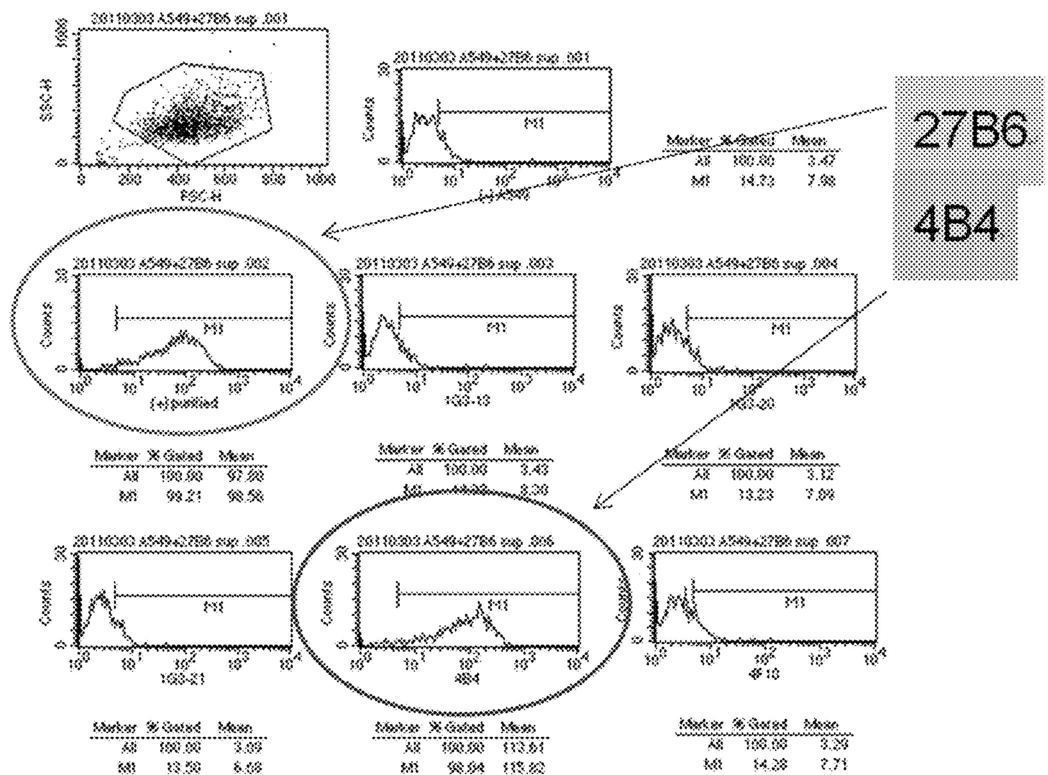

[Fig. 5]
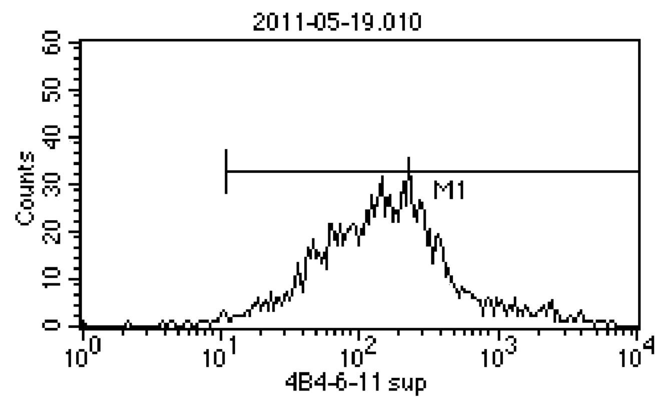
| Marker | % Gated | Mean |
|---|---|---|
| All | 100.00 | 256.07 |
| M1 | 99.48 | 257.35 |
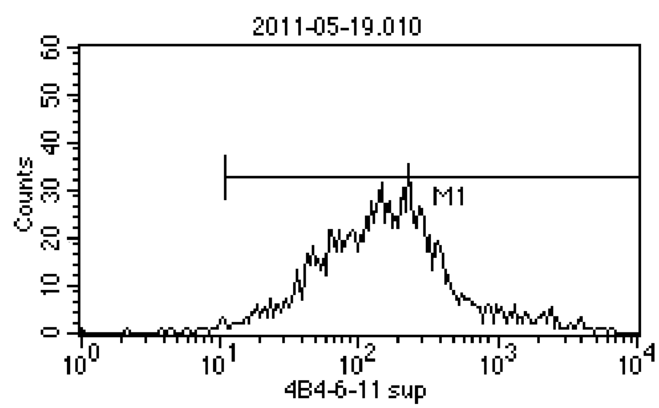
| Marker | % Gated | Mean |
|---|---|---|
| All | 100.00 | 256.07 |
| M1 | 99.48 | 257.35 |

[Fig. 6a]
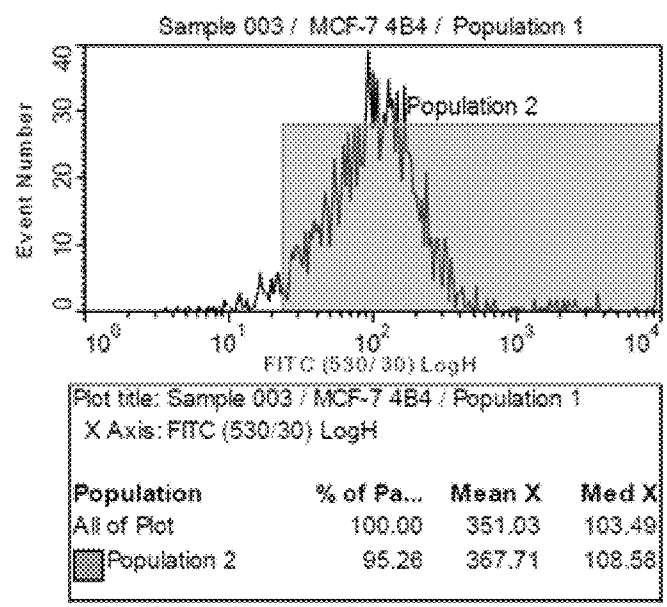
ER: Estrogen receptor
PR: Progesterone Receptor
HER2: human epidermal growth factor receptor 2

[Fig. 6b]
MDAMB231: triple negative
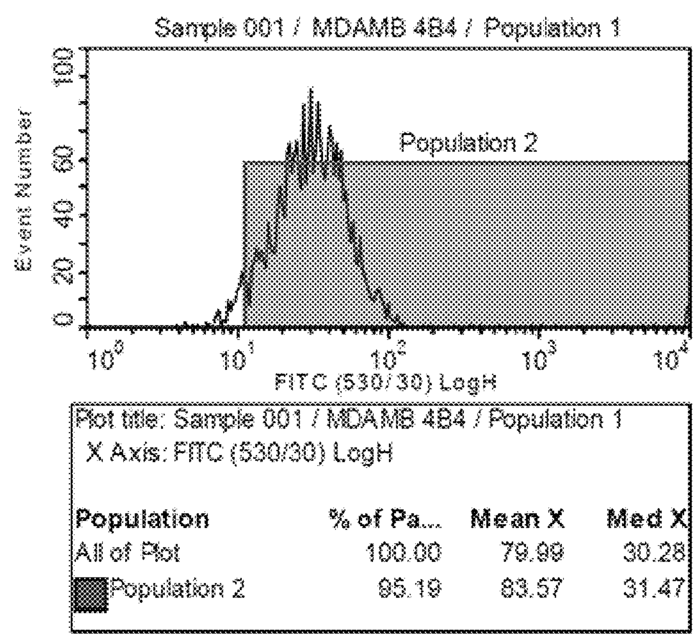
| Population | % of Pa... | Mean X | Med X |
|---|---|---|---|
| All of Plot | 100.00 | 79.99 | 30.28 |
| Population 2 | 95.19 | 83.57 | 31.47 |
ER: Estrogen receptor
PR: Progesterone Receptor
HER2: human epidermal growth factor receptor 2

[Fig. 6c]
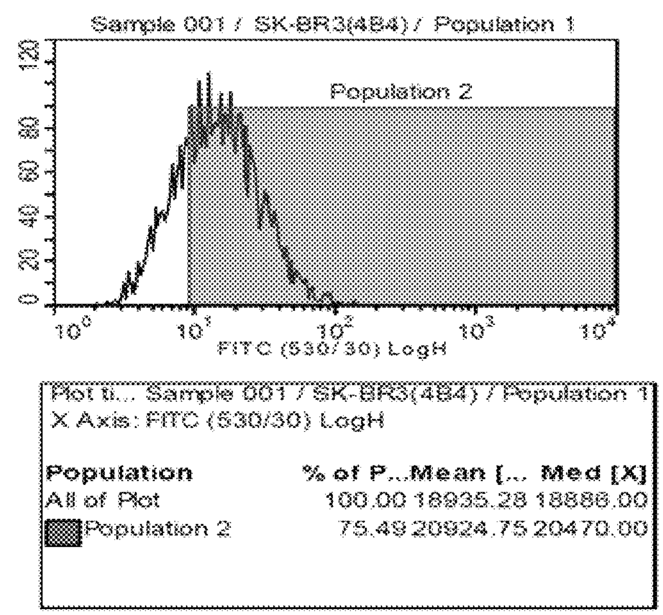
ER: Estrogen receptor
PR: Progesterone Receptor
HER2: human epidermal growth factor receptor 2

[Fig. 7]
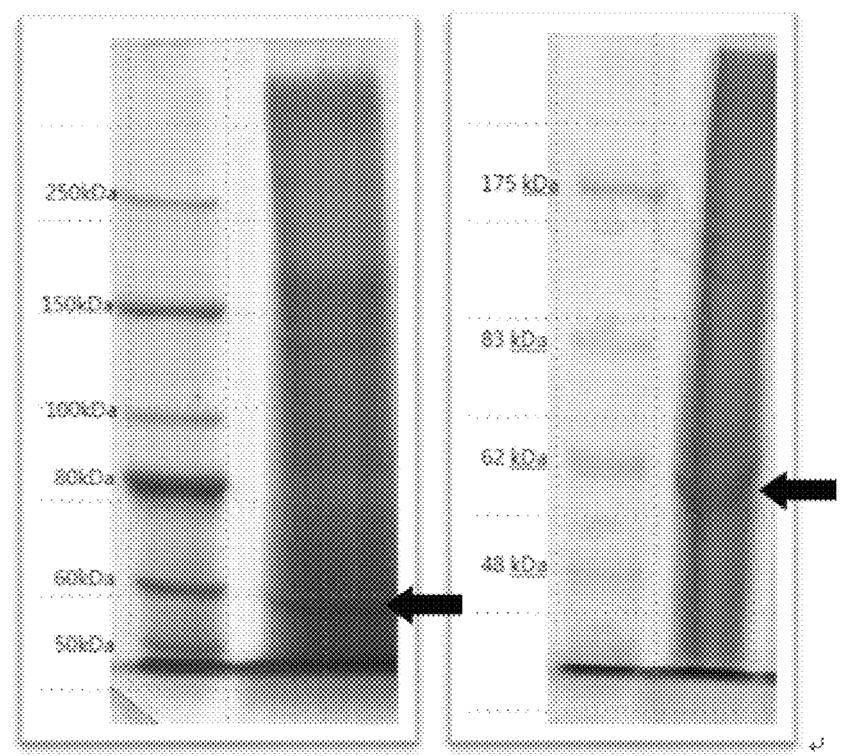

[Fig. 8]

| 4B4-60 | | | |
|---|---|---|---|
| No. | Description | mW(Da) | pI(pH) |
| 1 | Actin cytoplasmic 1 | 41739 | 5.16 |
| 2 | Carbonic anhydrase 12 | 39426 | 6.79 |
| 3 | Keratin type I cytoskeletal 9 | 62026 | 4.96 |
| 4 | Serum albumin | 68647 | 5.68 |
| 5 | Trypsin | 24393 | 6.91 |
| 6 | Actin 3 | 41813 | 5.01 |
| 7 | Actin 1 | 41648 | 5.24 |

| 27B6-60 | | | |
|---|---|---|---|
| No.1 | Description | mW(Da) | pI(pH) |
| 1 | Carbonic anhydrase 12 | 39426 | 6.79 |
| 2 | Pyruvate kinase isozymes M1/M2 | 58470 | 7.96 |
| 3 | Actin cytoskeletal 1 | 41814 | 5.24 |
| 4 | Retinal dehydrogenase 1 | 42327 | 5.08 |
| 5 | Hemoglobin subunit beta 1 | 15830 | 7.50 |
| 6 | Synaptic vesicle membrane protein VAT-1 homolog | 42122 | 5.88 |
| 7 | Protein disulfide-isomerase | 57146 | 5.98 |
| 8 | Serum albumin | 68647 | 5.68 |
| 9 | Trypsin | 24393 | 6.91 |
| 10 | Actin gamma | 41580 | 5.33 |

[Fig. 9]

| CA12 isoform 1 | MPRRSLHAAAVLLLVILKEQPSSPAPVNGSKWTYFGPDGENSWSKKYPSCGGLLQSPIDLHSDILQYDASLTPLEFQGYNLSANKQFLLTNNGHSVKLNLPSDMHIQGLQSRYSATQLHLHWGNPNDPHGSEHTVSGQHFAAELHIVHYNSDLYPDASTASNKSEGLAVLAVLIEMGSFNPSYDKIFSHLQHVKYKGQEAFVPGFNIEELLPERTAEYYRYRGSLTTPPCNPTVLWTVFRNPVQISQEQLLALETALYCTHMDDPSPR**EMINNFR**QVQKFDERLVYTSFSQVQVCTAAGLSLGIILSLALAGILGICIVVVVSIWLFRRKSIKKGDNK**GVIYKPATK**METEAHA | |
|---|---|---|
| 4B4 | QFLLTNNGHSVK | EMINNFR<br>GVIYKPATK |
| 27B6 | QFLLTNNGHSVK | WTYFGPDGENSWSK<br>YKGQEAFVPGFNIEELLPER<br>GQEAFVPGFNIEELLPER |

[Fig. 10]

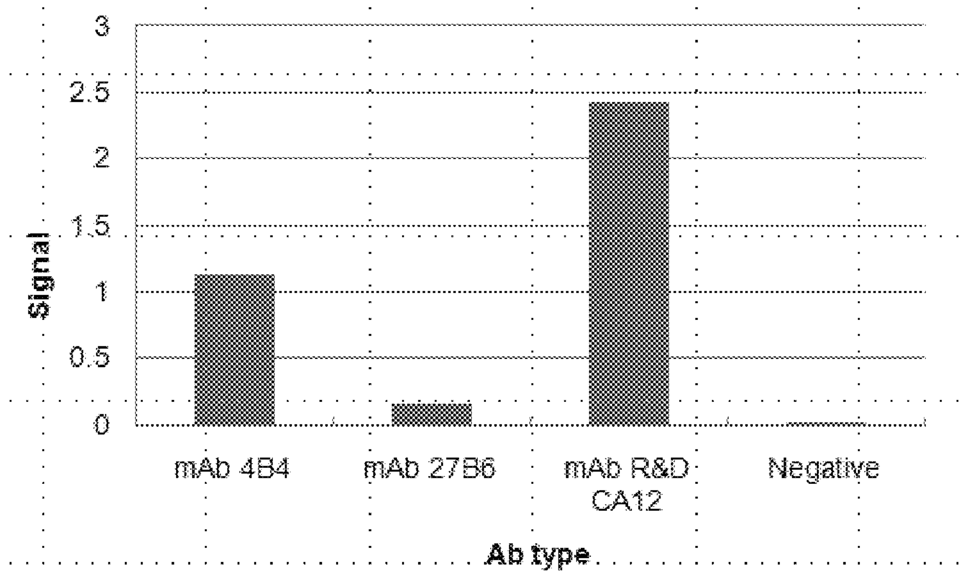

80 kDa
60 kDa
50 kDa
40 kDa
30 kDa

[Fig. 12]
| Capture antibody | Chimeric 27B6 | Chimeric 4B4 |
|---|---|---|
| Detector antibody | 4B4 mAb | 27B6 mAb |
| CA12 100ng/ml | 1.653 | 0,021 |
| CA12 50ng/ml | 1,349 | 0,016 |
| CA12 25ng/ml | 0,954 | 0,016 |
| CA12 12,5ng/ml | 0,634 | 0,011 |
| CA12 6;25ng/ml | 0,351 | 0,009 |
| CA12 3;13ng/ml | 0,193 | 0,008 |
| blank | 0,064 | 0,007 |
| blank | 0,055 | 0,008 |
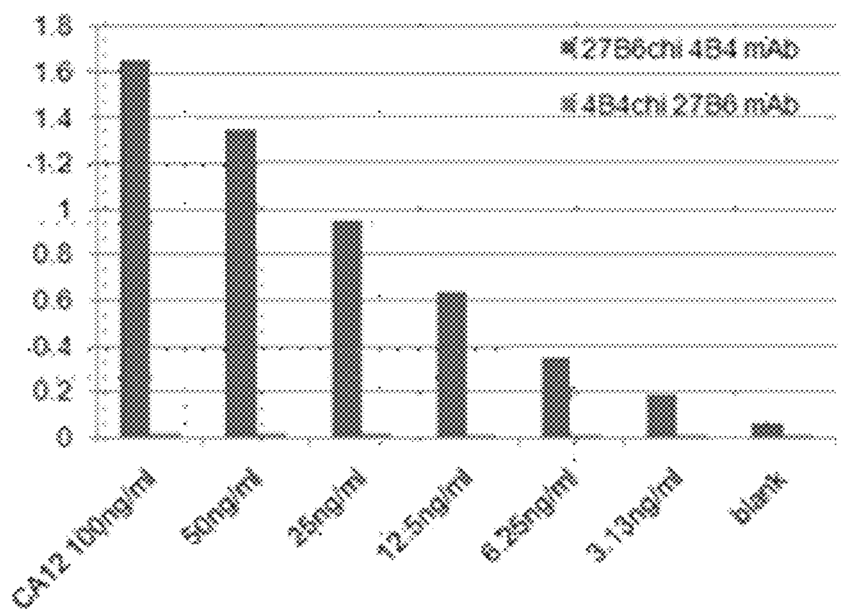

[Fig. 13]

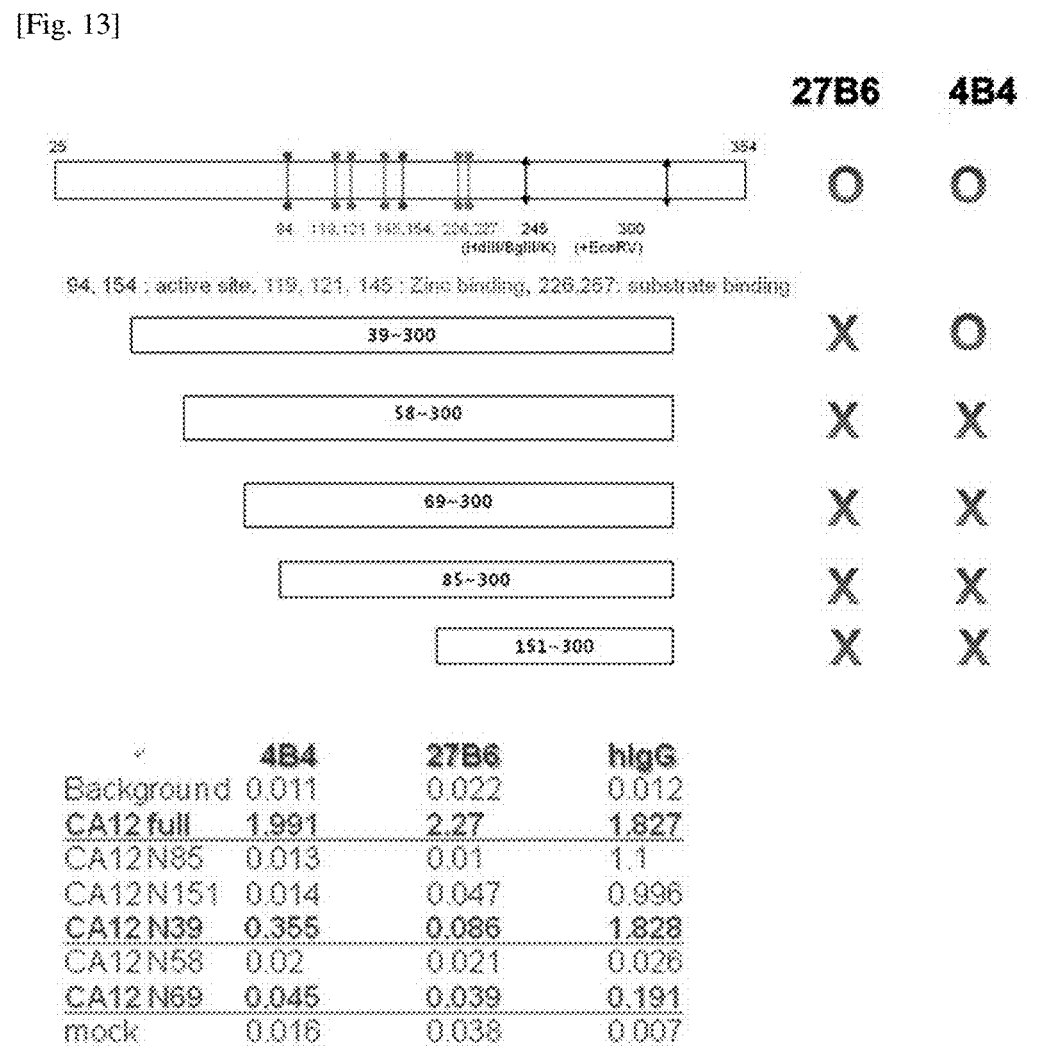

| | 27B6 | 4B4 |
|---|---|---|
| 39–354 (94, 119,121, 145,154, 226,227, 249 (HdIII/BglII/K), 300 (+EcoRV)) | O | O |
| 39~300 | X | O |
| 58~300 | X | X |
| 69~300 | X | X |
| 85~300 | X | X |
| 151~300 | X | X |

94, 154 : active site, 119, 121, 145 : Zinc binding, 226,267: substrate binding

| | 4B4 | 27B6 | hIgG |
|---|---|---|---|
| Background | 0.011 | 0.022 | 0.012 |
| CA12 full | 1.991 | 2.27 | 1.827 |
| CA12 N85 | 0.013 | 0.01 | 1.1 |
| CA12 N151 | 0.014 | 0.047 | 0.996 |
| CA12 N39 | 0.355 | 0.086 | 1.828 |
| CA12 N58 | 0.02 | 0.021 | 0.026 |
| CA12 N69 | 0.045 | 0.039 | 0.191 |
| mock | 0.016 | 0.038 | 0.007 |

[Fig. 14]
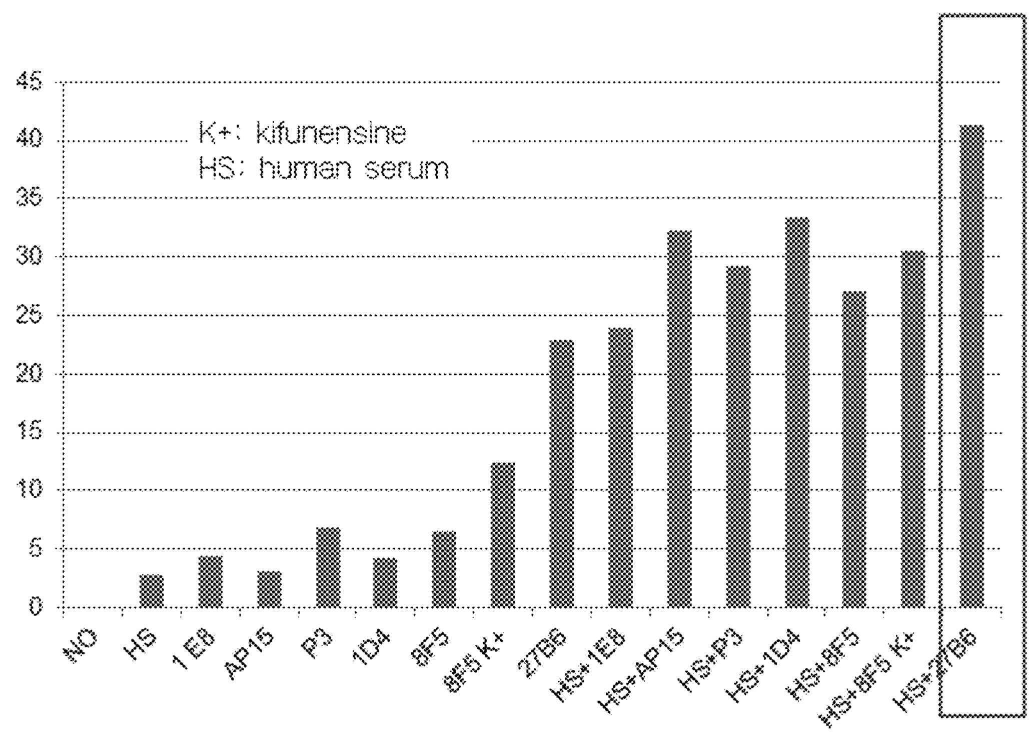

[Fig. 15]
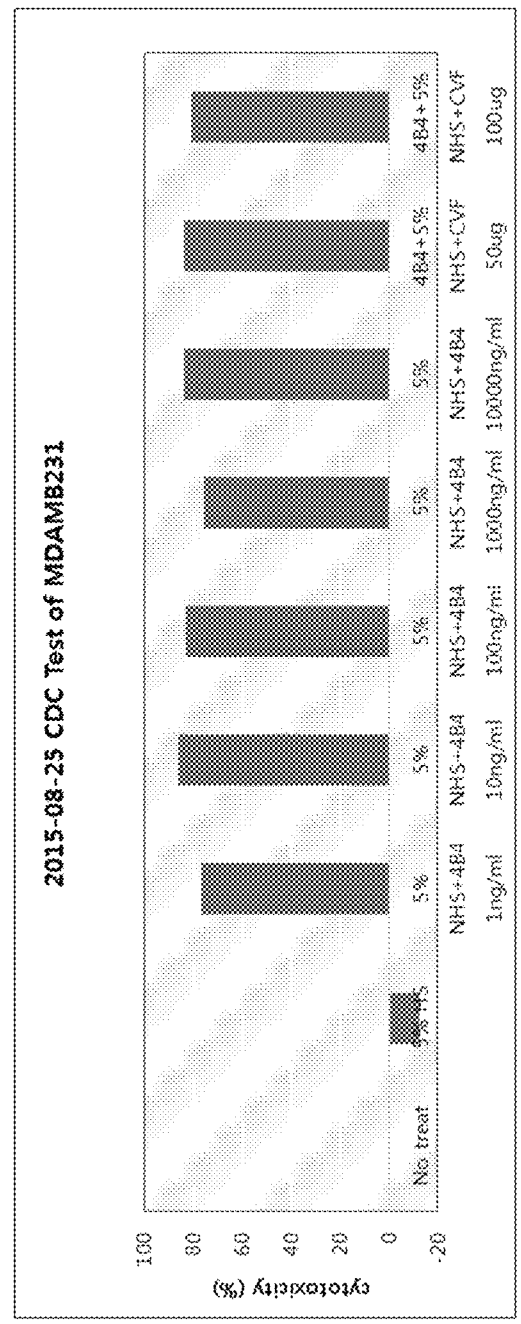

[Fig. 16]
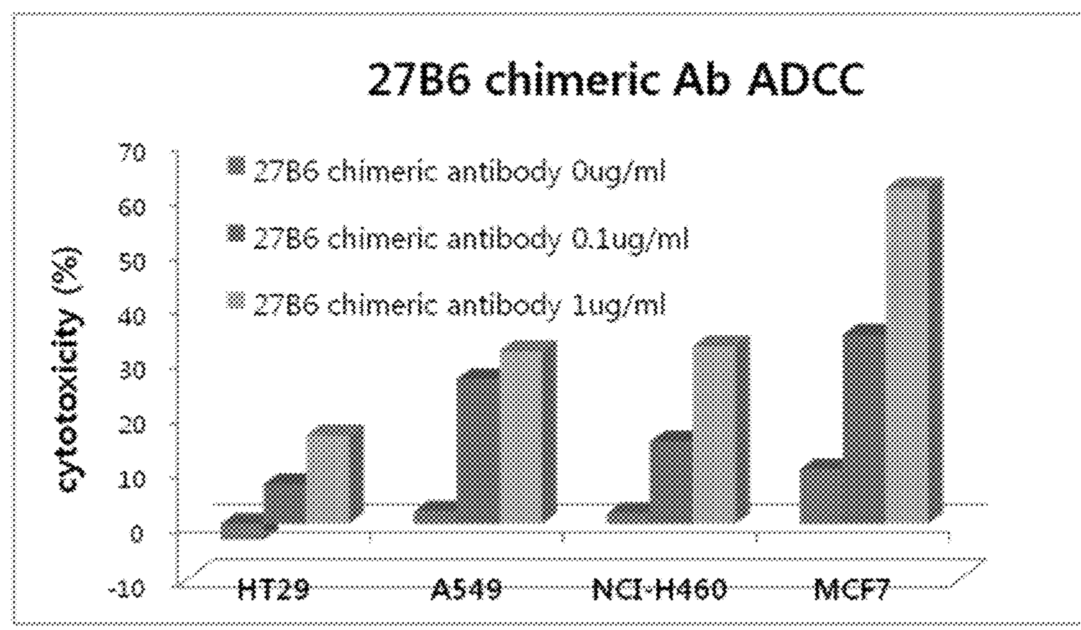

[Fig. 17]
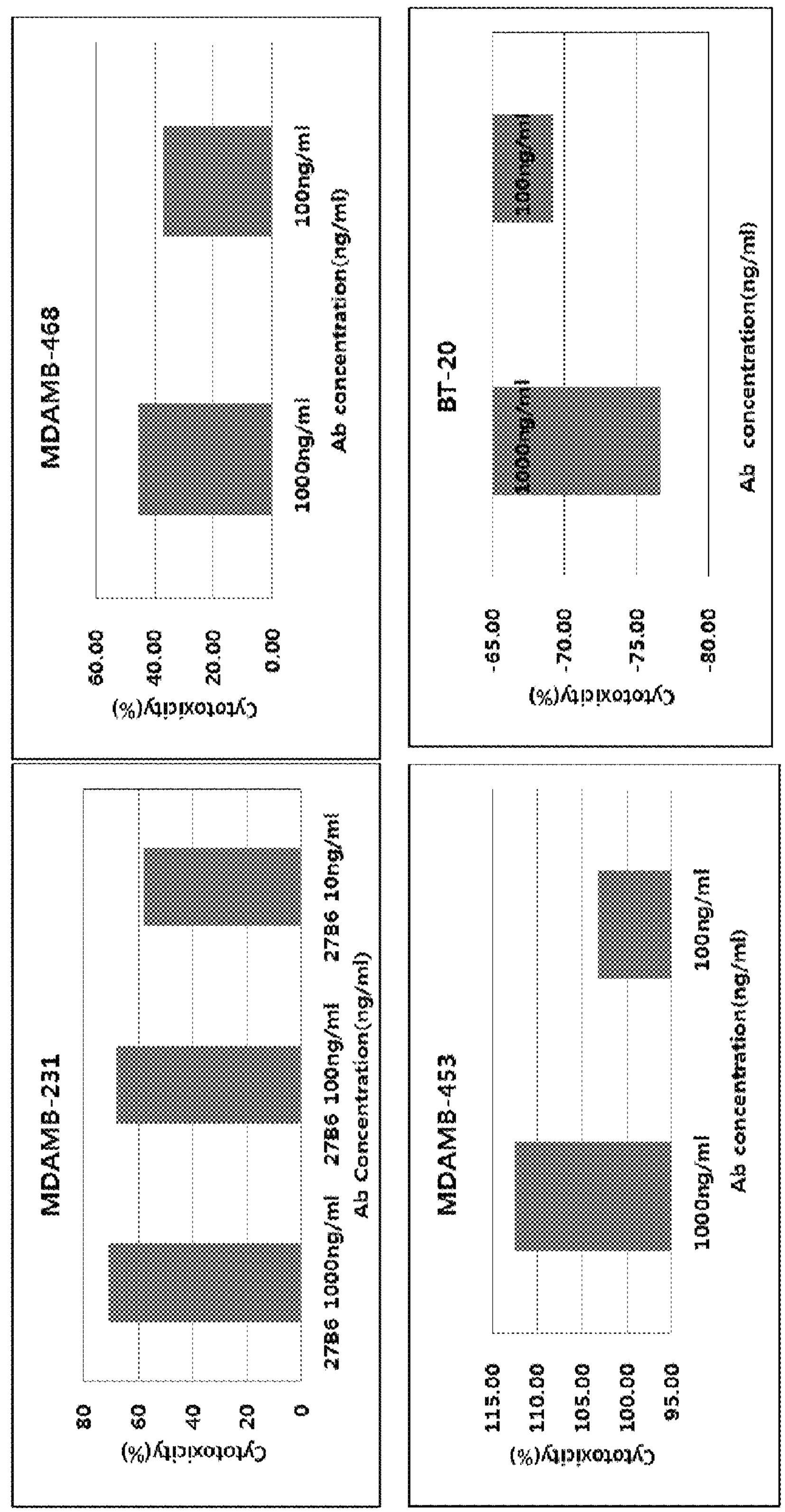

[Fig. 18]
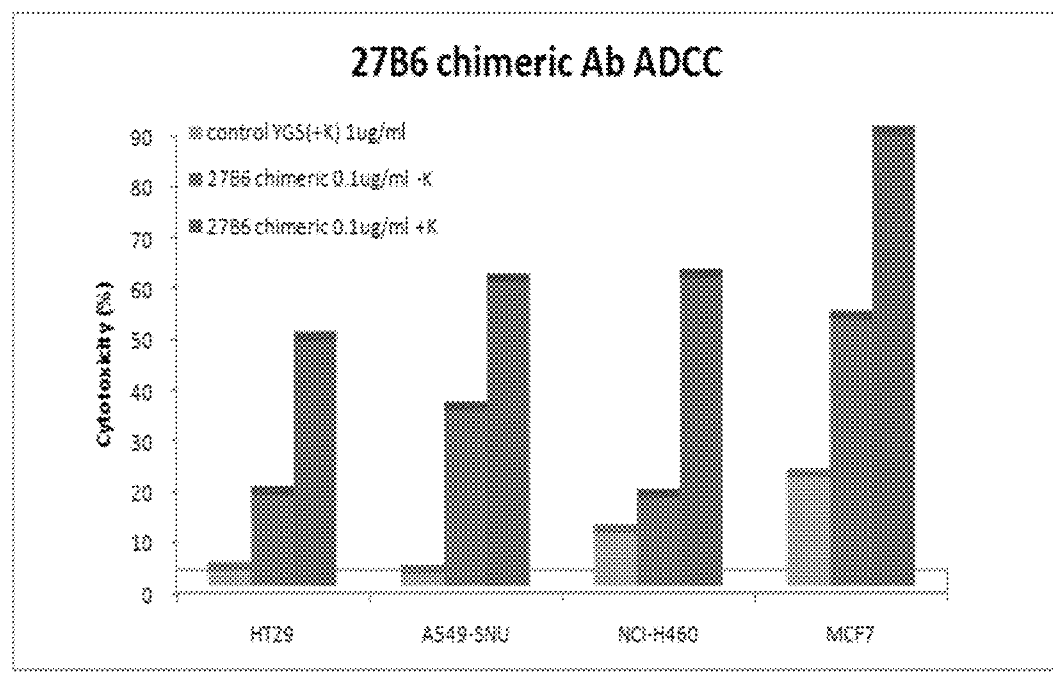
HT29: human colorectal adenocarcinoma
A549: human lung adenocarcinoma
NCI-H460: human non-small cell lung carcinoma
MCF7: human breast adenocarcinoma(ER+/ PR+/ ERBB2-)

[Fig. 19]
MDAMB231: triple negative
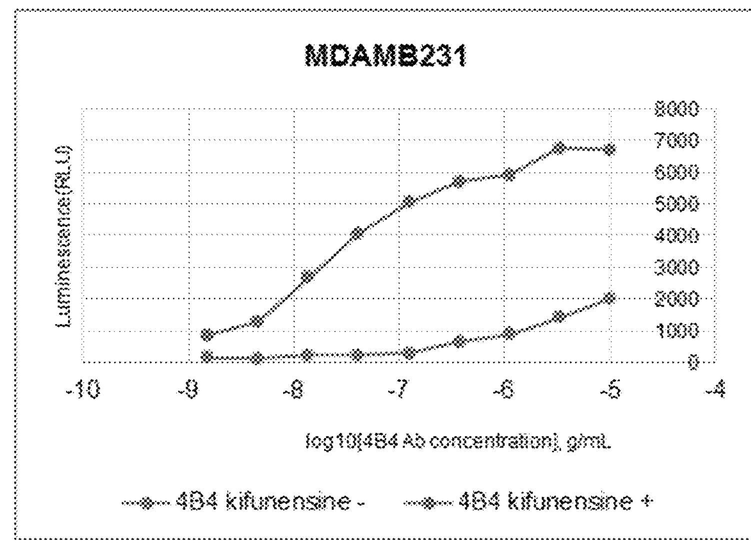
SKBR3: HER2+
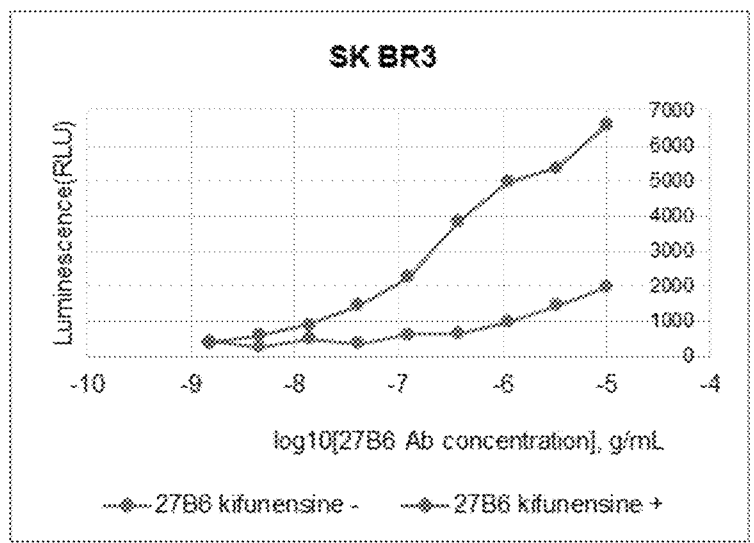
MDA-MB231: human breast adenocarcinoma(ER-/ PR-/ ERBB2-)
MCF7 :human breast adenocarcinoma(ER+/ PR+/ ERBB2-)

[Fig. 20]
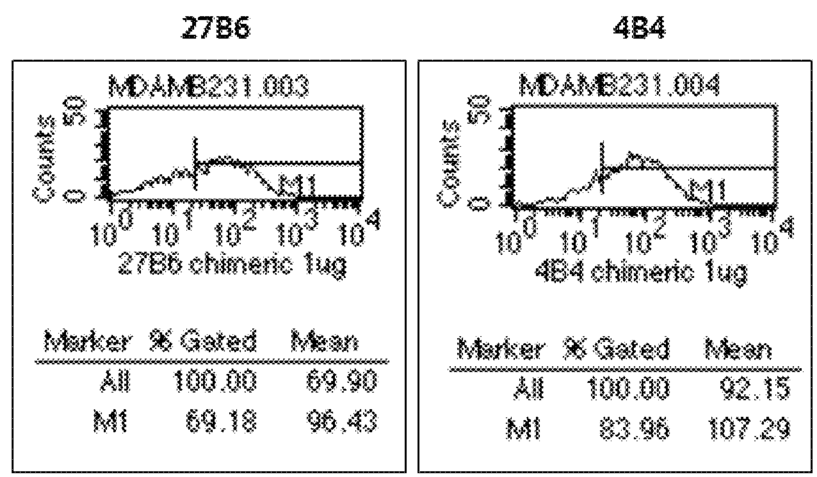

[Fig. 21]
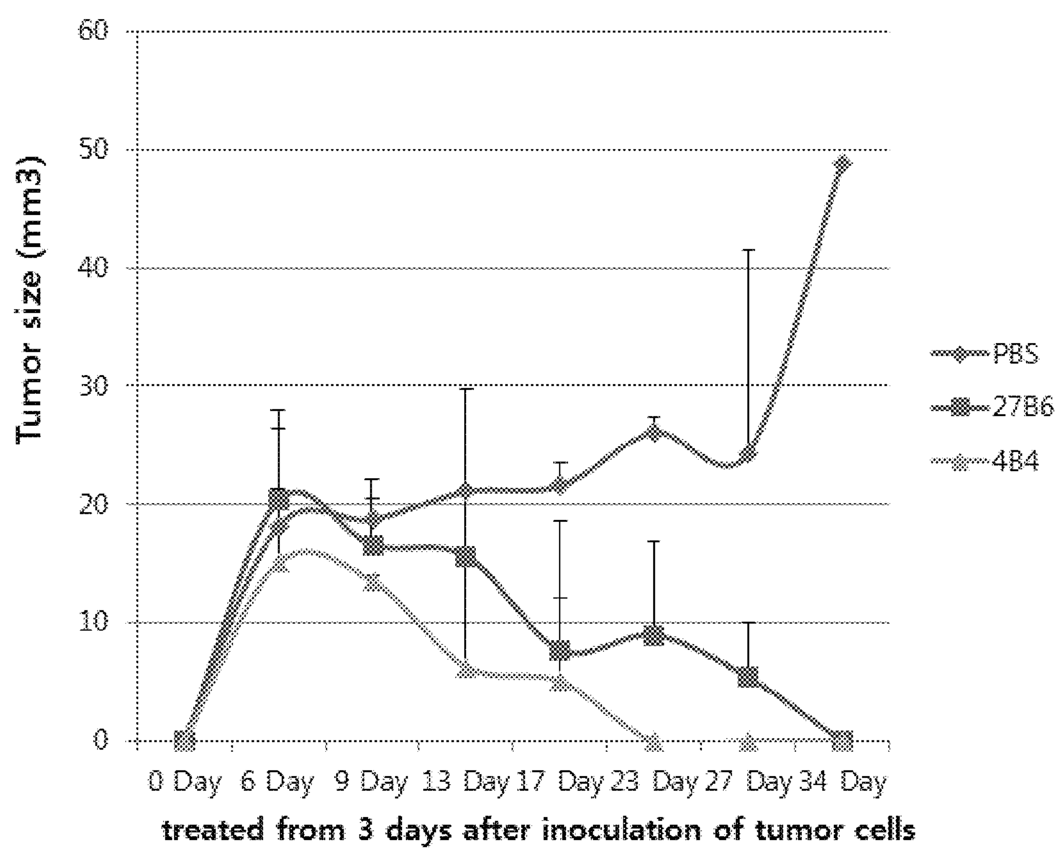

[Fig. 22]
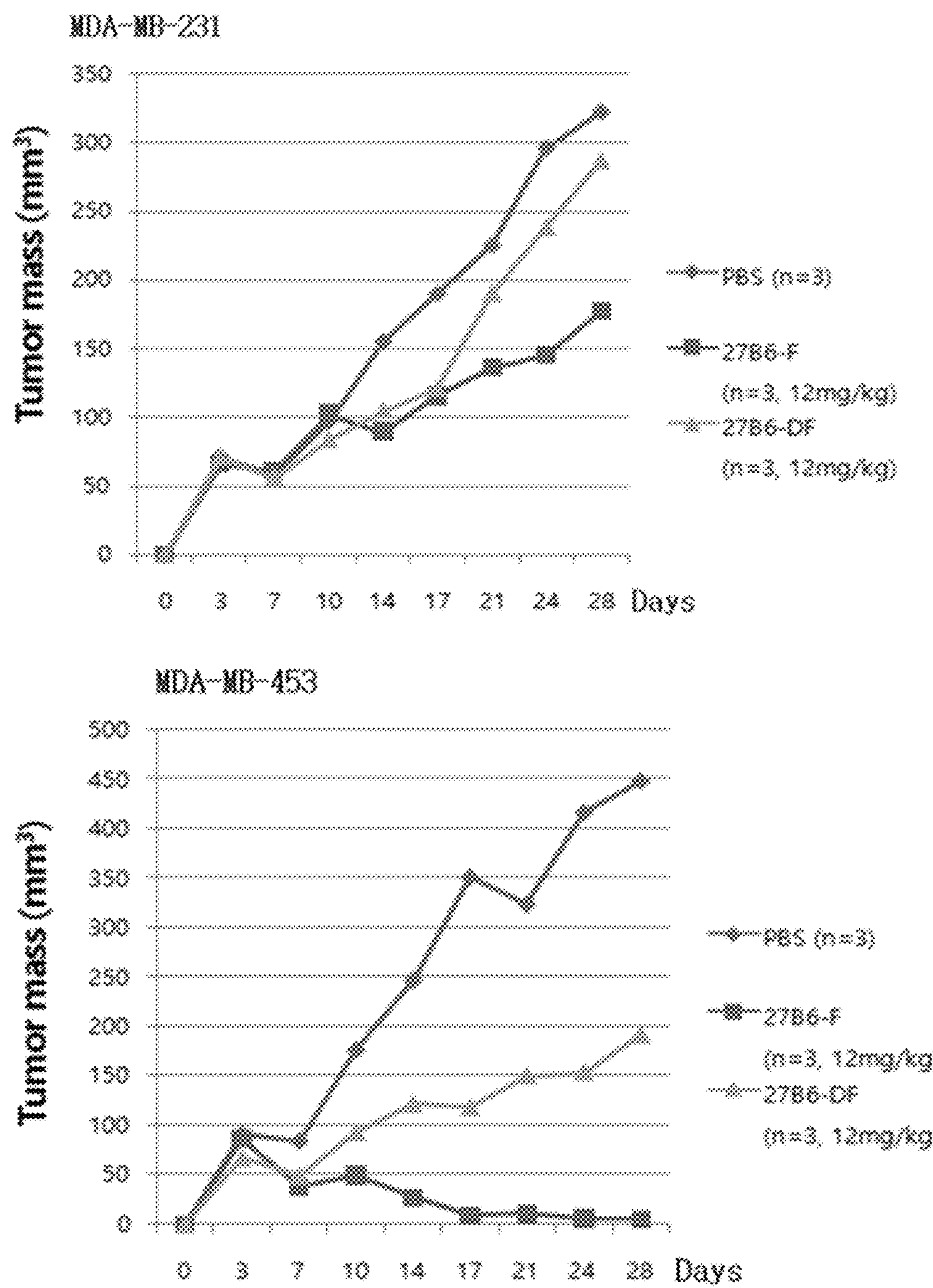

[Fig. 23]
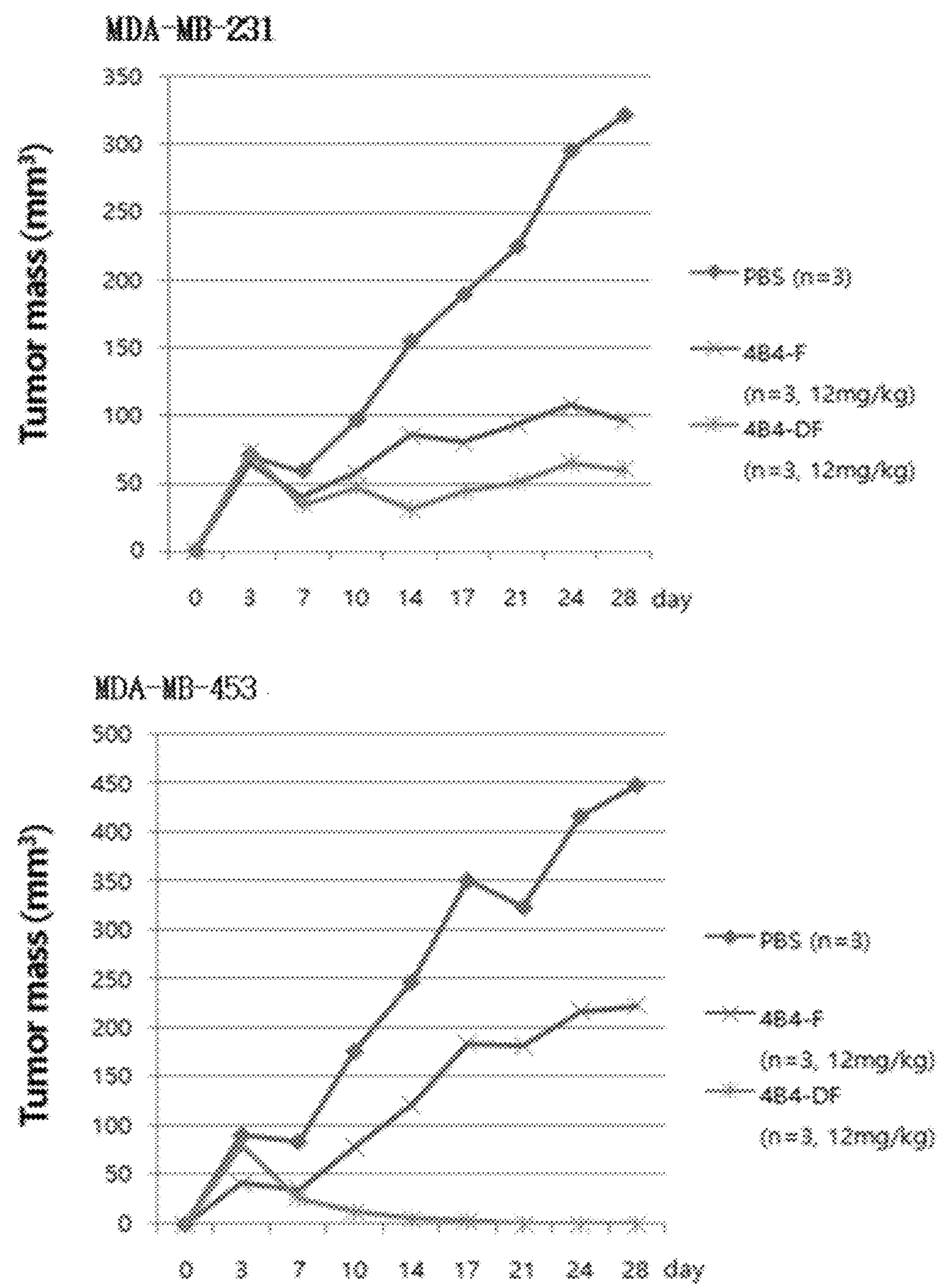

[Fig. 24]
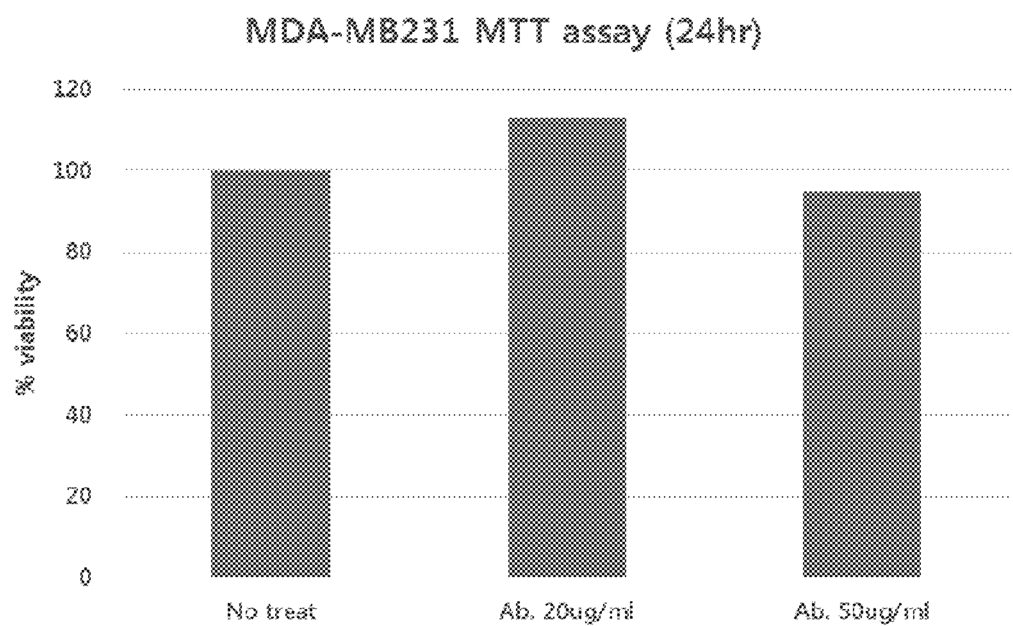

[Fig. 25]
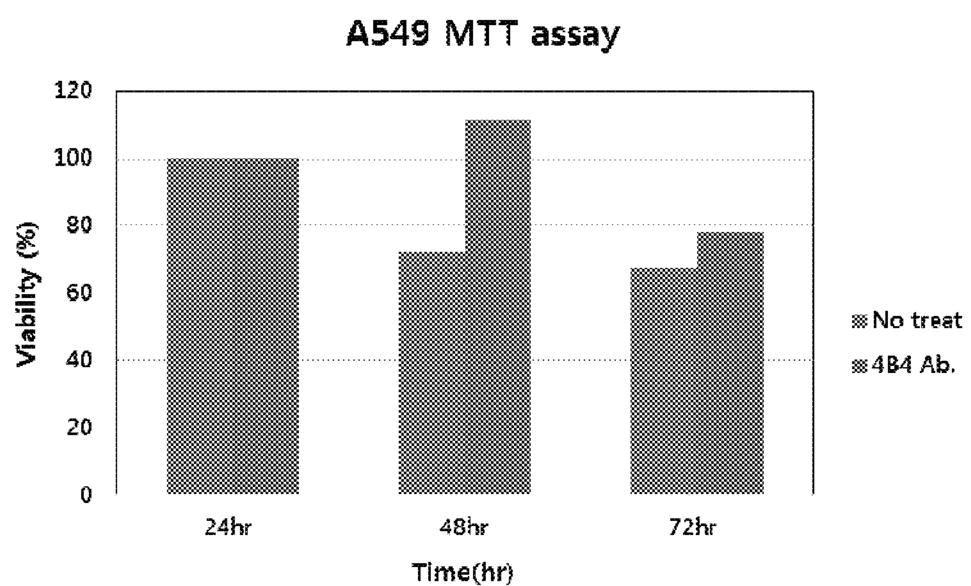

[Fig. 26]
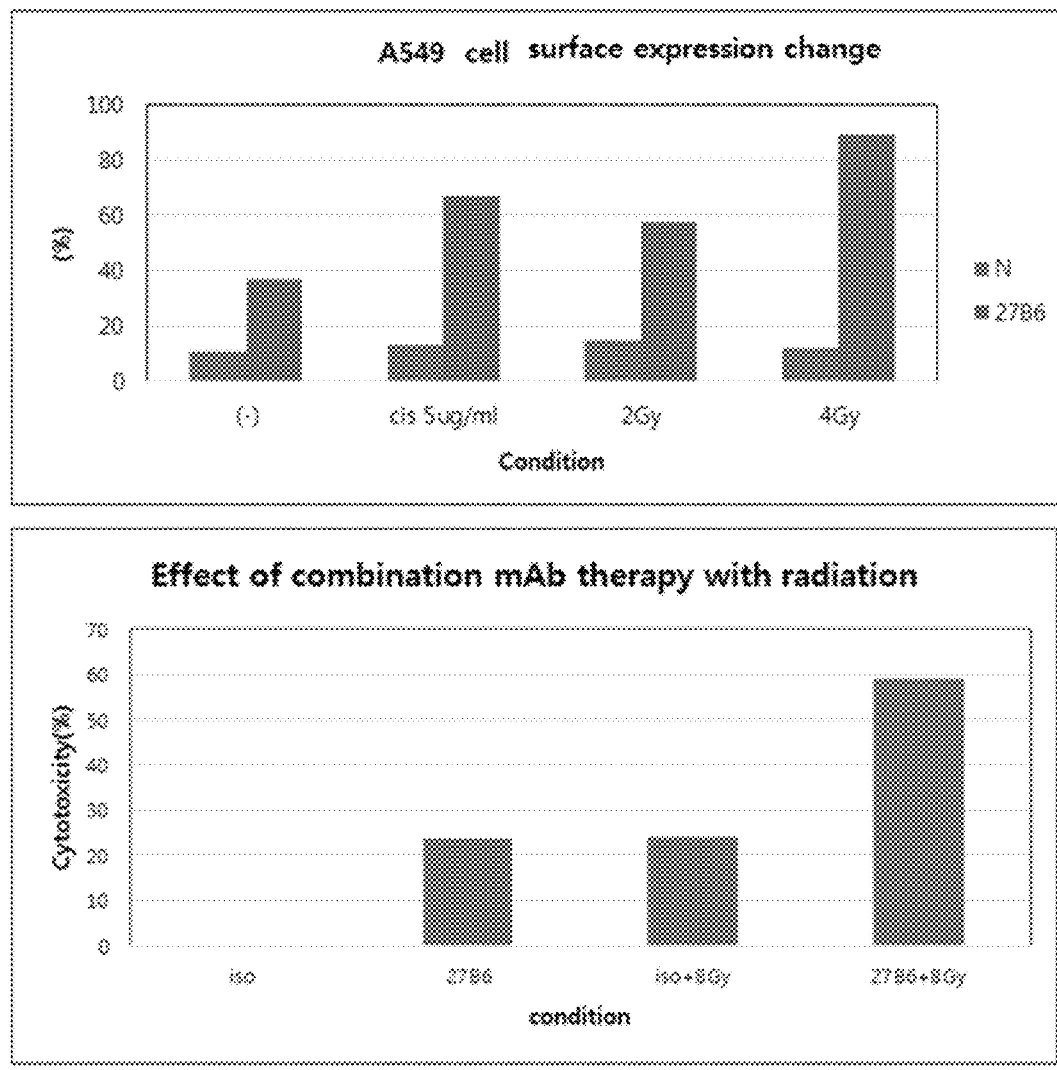

SEQUENCE LISTING

```
<160> NUMBER OF SEQ ID NOS: 27

<210> SEQ ID NO 1
<211> LENGTH: 7
<212> TYPE: PRT
<213> ORGANISM: Artificial Sequence
<220> FEATURE:
<223> OTHER INFORMATION: Epitope of Antibody  27B6

<400> SEQUENCE: 1

Trp Thr Tyr Phe Gly Pro Asp
1               5


<210> SEQ ID NO 2
<211> LENGTH: 14
<212> TYPE: PRT
<213> ORGANISM: Artificial Sequence
<220> FEATURE:
<223> OTHER INFORMATION: Epitope of Antibody  27B6

<400> SEQUENCE: 2

Ala Pro Val Asn Gly Ser Lys Trp Thr Tyr Phe Gly Pro Asp
1               5                   10


<210> SEQ ID NO 3
<211> LENGTH: 14
<212> TYPE: PRT
<213> ORGANISM: Artificial Sequence
<220> FEATURE:
<223> OTHER INFORMATION: Epitope of Antibody  4B4

<400> SEQUENCE: 3

Gly Glu Asn Ser Trp Ser Lys Lys Tyr Pro Ser Cys Gly Gly
1               5                   10


<210> SEQ ID NO 4
<211> LENGTH: 19
<212> TYPE: PRT
<213> ORGANISM: Artificial Sequence
<220> FEATURE:
<223> OTHER INFORMATION: Epitope of Antibody  4B4

<400> SEQUENCE: 4

Gly Glu Asn Ser Trp Ser Lys Lys Tyr Pro Ser Cys Gly Gly Leu Leu
1               5                   10                  15

Gln Ser Pro


<210> SEQ ID NO 5
<211> LENGTH: 354
<212> TYPE: PRT
<213> ORGANISM: Artificial Sequence
<220> FEATURE:
<223> OTHER INFORMATION: Carbonic anhydrase XII

<400> SEQUENCE: 5

Met Pro Arg Arg Ser Leu His Ala Ala Ala Val Leu Leu Leu Val Ile
1               5                   10                  15

Leu Lys Glu Gln Pro Ser Ser Pro Ala Pro Val Asn Gly Ser Lys Trp
            20                  25                  30

Thr Tyr Phe Gly Pro Asp Gly Glu Asn Ser Trp Ser Lys Lys Tyr Pro
        35                  40                  45

Ser Cys Gly Gly Leu Leu Gln Ser Pro Ile Asp Leu His Ser Asp Ile
    50                  55                  60

Leu Gln Tyr Asp Ala Ser Leu Thr Pro Leu Glu Phe Gln Gly Tyr Asn
```

```
65                  70                  75                  80

Leu Ser Ala Asn Lys Gln Phe Leu Leu Thr Asn Asn Gly His Ser Val
                85                  90                  95

Lys Leu Asn Leu Pro Ser Asp Met His Ile Gln Gly Leu Gln Ser Arg
            100                 105                 110

Tyr Ser Ala Thr Gln Leu His Leu His Trp Gly Asn Pro Asn Asp Pro
        115                 120                 125

His Gly Ser Glu His Thr Val Ser Gly Gln His Phe Ala Ala Glu Leu
    130                 135                 140

His Ile Val His Tyr Asn Ser Asp Leu Tyr Pro Asp Ala Ser Thr Ala
145                 150                 155                 160

Ser Asn Lys Ser Glu Gly Leu Ala Val Leu Ala Val Leu Ile Glu Met
                165                 170                 175

Gly Ser Phe Asn Pro Ser Tyr Asp Lys Ile Phe Ser His Leu Gln His
            180                 185                 190

Val Lys Tyr Lys Gly Gln Glu Ala Phe Val Pro Gly Phe Asn Ile Glu
        195                 200                 205

Glu Leu Leu Pro Glu Arg Thr Ala Glu Tyr Tyr Arg Tyr Arg Gly Ser
    210                 215                 220

Leu Thr Thr Pro Pro Cys Asn Pro Thr Val Leu Trp Thr Val Phe Arg
225                 230                 235                 240

Asn Pro Val Gln Ile Ser Gln Glu Gln Leu Leu Ala Leu Glu Thr Ala
                245                 250                 255

Leu Tyr Cys Thr His Met Asp Asp Pro Ser Pro Arg Glu Met Ile Asn
            260                 265                 270

Asn Phe Arg Gln Val Gln Lys Phe Asp Glu Arg Leu Val Tyr Thr Ser
        275                 280                 285

Phe Ser Gln Val Gln Val Cys Thr Ala Ala Gly Leu Ser Leu Gly Ile
    290                 295                 300

Ile Leu Ser Leu Ala Leu Ala Gly Ile Leu Gly Ile Cys Ile Val Val
305                 310                 315                 320

Val Val Ser Ile Trp Leu Phe Arg Arg Lys Ser Ile Lys Lys Gly Asp
                325                 330                 335

Asn Lys Gly Val Ile Tyr Lys Pro Ala Thr Lys Met Glu Thr Glu Ala
            340                 345                 350

His Ala


<210> SEQ ID NO 6
<211> LENGTH: 8
<212> TYPE: PRT
<213> ORGANISM: Artificial Sequence
<220> FEATURE:
<223> OTHER INFORMATION: VH CDR1 of antibody 27B6

<400> SEQUENCE: 6

Gly Tyr Ser Phe Thr Asn Tyr Trp
1               5


<210> SEQ ID NO 7
<211> LENGTH: 8
<212> TYPE: PRT
<213> ORGANISM: Artificial Sequence
<220> FEATURE:
<223> OTHER INFORMATION: VH CDR2 of antibody 27B6

<400> SEQUENCE: 7

Ile Asp Pro Ser Asp Ser Glu Thr
```

```
1               5


<210> SEQ ID NO 8
<211> LENGTH: 13
<212> TYPE: PRT
<213> ORGANISM: Artificial Sequence
<220> FEATURE:
<223> OTHER INFORMATION: VH CDR3 of antibody 27B6

<400> SEQUENCE: 8

Thr Arg Gly Ile Arg Gly Gly Tyr Tyr Ala Met Asp Tyr
1               5                   10


<210> SEQ ID NO 9
<211> LENGTH: 6
<212> TYPE: PRT
<213> ORGANISM: Artificial Sequence
<220> FEATURE:
<223> OTHER INFORMATION: VL CDR1 of antibody 27B6

<400> SEQUENCE: 9

Gln Asp Ile Ser Asn Tyr
1               5


<210> SEQ ID NO 10
<211> LENGTH: 3
<212> TYPE: PRT
<213> ORGANISM: Artificial Sequence
<220> FEATURE:
<223> OTHER INFORMATION: VL CDR2 of antibody 27B6

<400> SEQUENCE: 10

Tyr Thr Ser
1


<210> SEQ ID NO 11
<211> LENGTH: 9
<212> TYPE: PRT
<213> ORGANISM: Artificial Sequence
<220> FEATURE:
<223> OTHER INFORMATION: VL CDR3 of antibody 27B6

<400> SEQUENCE: 11

Gln Gln Gly Asp Thr Leu Pro Arg Thr
1               5


<210> SEQ ID NO 12
<211> LENGTH: 120
<212> TYPE: PRT
<213> ORGANISM: Artificial Sequence
<220> FEATURE:
<223> OTHER INFORMATION: Heavy chain variable region of antibody 27B6

<400> SEQUENCE: 12

Gln Val Gln Leu Gln Gln Ser Gly Pro Gln Leu Val Trp Pro Gly Ala
1               5                   10                  15

Ser Val Lys Ile Ser Cys Asn Thr Ser Gly Tyr Ser Phe Thr Asn Tyr
            20                  25                  30

Trp Ile His Trp Val Lys Gln Arg Pro Gly Gln Gly Leu Glu Trp Ile
        35                  40                  45

Gly Met Ile Asp Pro Ser Asp Ser Glu Thr Arg Leu Asn Gln Lys Phe
    50                  55                  60

Lys Asp Lys Thr Thr Leu Thr Val Asp Arg Ser Ser Ser Thr Ala Tyr
65                  70                  75                  80
```

-continued

```
Met Gln Val Ser Ser Ser Thr Ser Glu Asp Ser Ala Val Tyr Tyr Cys
                85                  90                  95

Thr Arg Gly Ile Arg Gly Gly Tyr Tyr Ala Met Asp Tyr Trp Gly Gln
            100                 105                 110

Gly Thr Ser Val Thr Val Ser Ser
        115                 120


<210> SEQ ID NO 13
<211> LENGTH: 107
<212> TYPE: PRT
<213> ORGANISM: Artificial Sequence
<220> FEATURE:
<223> OTHER INFORMATION: Light chain variable region of antibody 27B6

<400> SEQUENCE: 13

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Glu Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Arg
                85                  90                  95

Thr Phe Gly Glu Gly Thr Lys Leu Glu Ile Arg
            100                 105


<210> SEQ ID NO 14
<211> LENGTH: 8
<212> TYPE: PRT
<213> ORGANISM: Artificial Sequence
<220> FEATURE:
<223> OTHER INFORMATION: VH CDR1 of antibody 4B4

<400> SEQUENCE: 14

Gly Tyr Ser Tyr Thr Asp Tyr Asn
1               5


<210> SEQ ID NO 15
<211> LENGTH: 8
<212> TYPE: PRT
<213> ORGANISM: Artificial Sequence
<220> FEATURE:
<223> OTHER INFORMATION: VH CDR2 of antibody 4B4

<400> SEQUENCE: 15

Ile Asp Pro Ala Asn Gly Asp Thr
1               5


<210> SEQ ID NO 16
<211> LENGTH: 14
<212> TYPE: PRT
<213> ORGANISM: Artificial Sequence
<220> FEATURE:
<223> OTHER INFORMATION: VH CDR3 of antibody 4B4

<400> SEQUENCE: 16

Ala Arg Pro Ile Tyr Tyr Gly Val Tyr Trp Tyr Phe Asp Val
1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: VL CDR1 of antibody 4B4

<400> SEQUENCE: 17

```
Lys Ser Leu Leu His Ser Asn Gly Asn Thr Tyr
1               5                   10
```

<210> SEQ ID NO 18
<211> LENGTH: 3
<212> TYPE: PRT
<213> ORGANISM: Artificial Sequence
<220> FEATURE:
<223> OTHER INFORMATION: VL CDR2 of antibody 4B4

<400> SEQUENCE: 18

```
Arg Met Ser
1
```

<210> SEQ ID NO 19
<211> LENGTH: 9
<212> TYPE: PRT
<213> ORGANISM: Artificial Sequence
<220> FEATURE:
<223> OTHER INFORMATION: VL CDR3 of antibody 4B4

<400> SEQUENCE: 19

```
Met Gln His Leu Glu Tyr Pro Phe Thr
1               5
```

<210> SEQ ID NO 20
<211> LENGTH: 120
<212> TYPE: PRT
<213> ORGANISM: Artificial Sequence
<220> FEATURE:
<223> OTHER INFORMATION: Heavy chain variable region of antibody 4B4

<400> SEQUENCE: 20

```
Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Ser Tyr Thr Asp Tyr
            20                  25                  30

Asn Ile Tyr Trp Val Arg Gln Ser Gln Gly Lys Ser Leu Asp Trp Ile
        35                  40                  45

Gly Tyr Ile Asp Pro Ala Asn Gly Asp Thr Thr Tyr Asn Gln Lys Phe
    50                  55                  60

Lys Gly Lys Ala Thr Leu Thr Val Asp Lys Ser Ser Ser Thr Ala Phe
65                  70                  75                  80

Met His Leu Asn Ser Leu Thr Ser Asp Gly Ser Ala Val Tyr Phe Cys
                85                  90                  95

Ala Arg Pro Ile Tyr Tyr Gly Val Tyr Trp Tyr Phe Asp Val Trp Gly
            100                 105                 110

Ala Gly Thr Thr Val Thr Val Ser
        115                 120
```

<210> SEQ ID NO 21
<211> LENGTH: 112
<212> TYPE: PRT
<213> ORGANISM: Artificial Sequence
<220> FEATURE:

<223> OTHER INFORMATION: Light chain variable region of antibody 4B4

<400> SEQUENCE: 21

```
Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110
```

<210> SEQ ID NO 22
<211> LENGTH: 12
<212> TYPE: PRT
<213> ORGANISM: Artificial Sequence
<220> FEATURE:
<223> OTHER INFORMATION: Binding fragment of antibody 27B6 and antibody 4B4 obtained by MS analysis

<400> SEQUENCE: 22

```
Gln Phe Leu Leu Thr Asn Asn Gly His Ser Val Lys
1               5                   10
```

<210> SEQ ID NO 23
<211> LENGTH: 14
<212> TYPE: PRT
<213> ORGANISM: Artificial Sequence
<220> FEATURE:
<223> OTHER INFORMATION: Binding fragment of antibody 27B6 obtained by MS analysis

<400> SEQUENCE: 23

```
Trp Thr Tyr Phe Gly Pro Asp Gly Glu Asn Ser Trp Ser Lys
1               5                   10
```

<210> SEQ ID NO 24
<211> LENGTH: 18
<212> TYPE: PRT
<213> ORGANISM: Artificial Sequence
<220> FEATURE:
<223> OTHER INFORMATION: Binding fragment of antibody 27B6 obtained by MS analysis

<400> SEQUENCE: 24

```
Gly Gln Glu Ala Phe Val Pro Gly Phe Asn Ile Glu Glu Leu Leu Pro
1               5                   10                  15

Glu Arg
```

<210> SEQ ID NO 25
<211> LENGTH: 20
<212> TYPE: PRT
<213> ORGANISM: Artificial Sequence
<220> FEATURE:
<223> OTHER INFORMATION: Binding fragment of antibody 27B6 obtained by MS analysis

<400> SEQUENCE: 25

```
Tyr Lys Gly Gln Glu Ala Phe Val Pro Gly Phe Asn Ile Glu Glu Leu
1               5                   10                  15

Leu Pro Glu Arg
            20


<210> SEQ ID NO 26
<211> LENGTH: 7
<212> TYPE: PRT
<213> ORGANISM: Artificial Sequence
<220> FEATURE:
<223> OTHER INFORMATION: Binding fragment of antibody 4B4 obtained by MS
      analysis

<400> SEQUENCE: 26

Glu Met Ile Asn Asn Phe Arg
1               5


<210> SEQ ID NO 27
<211> LENGTH: 9
<212> TYPE: PRT
<213> ORGANISM: Artificial Sequence
<220> FEATURE:
<223> OTHER INFORMATION: Binding fragment of antibody 4B4 obtained by MS
      analysis

<400> SEQUENCE: 27

Gly Val Ile Tyr Lys Pro Ala Thr Lys
1               5
```

ANTIBODY BINDING TO CARBONIC ANHYDRASE AND USE THEREOF

CROSS-REFERENCES TO RELATED APPLICATION

This application is a Division Application of U.S. patent application Ser. No. 15/344,764 filed on Nov. 7, 2016, which is a Continuation-in-part Application of PCT Patent Application No. application of PCT/KR2016/005722 filed on May 30, 2016, the contents of which are incorporated herein by reference.

TECHNICAL FIELD

The present disclosure relates to an antibody that recognizes and binds to carbonic anhydrase, a nucleic acid molecule coding for the antibody or an antigen-binding fragment, a vector carrying the nucleic acid molecule, a host cell including the nucleic acid molecule or the vector, and use of the antibody or an antigen-binding fragment thereof in the alleviation, prevention, treatment or diagnosis of solid tumors.

BACKGROUND ART

Carbonic anhydrase (CA) form a family of enzymes that catalyze the rapid interconversion of carbon dioxide and water to bicarbonate and proton or vice versa to maintain pH homeostasis in the body. The active site of most carbonic anhydrases contains a zinc ion; they are therefore classified as metalloenzymes.

The family of carbonic anhydrases has several members. There are at least five distinct CA families (α, β, γ, δ and ε). The α-CAs are found in mammals. The α-CAs are divided into four broad subgroups, which, in turn, consist of several isoforms: cytosolic CAs (CA-I, CA-II, CA III, CA-VII, and CA-XIII), mitochondrial CAs (CA-VA and CA-VB), secreted CAs (CA-VI), and membrane-associated CAs (CA-IV, CA-IX, CA-XII, CA-XIV, and CA-XV).

CA isozymes II, IX and XII have been associated with neoplastic processes, and they are potential histological and prognostic biomarkers of certain tumors [Nordfors et al. (2010), BMC cancer; 10:148]. CA-II is the most widely expressed member of the α-CA gene family, being present in virtually every human tissue and organ. The transmembrane enzyme, CA-IX, was first recognized as a novel tumor-associated antigen expressed in several types of human carcinomas as well as in normal gastrointestinal tissue. CA-IX has been functionally linked to cell adhesion, differentiation, proliferation and oncogenic processes, and its enzymatic activity is comparable to CA II. Another transmembrane CA isozyme, CA-XII, was first found in normal kidney tissue and renal cell carcinoma. Further studies have shown that it is expressed in several other tumors (Ulmasov et al. (2000)), but also in some normal organs such as the colon and uterus. High expression of CA-II, CA-IX and CA-XII in tumors, particularly under hypoxic conditions, has further suggested that these enzymes may functionally participate in the invasion process, which is facilitated by acidification of the extracellular space.

DISCLOSURE

Technical Problem

In accordance with an embodiment thereof, the present disclosure addresses an antibody binding to carbonic anhydrase, and an antigen-binding fragment thereof.

Another embodiment of the present disclosure relates to a nucleic acid molecule encoding the antibody or the antigen-binding fragment, a vector carrying the nucleic acid molecule, and a host cell including the nucleic acid molecule.

A further embodiment of the present invention relates to a method or a kit for detecting or diagnosing a carbonic anhydrase-associated disease, comprising the antibody, the nucleic acid molecule, the vector, and/or the host cell.

Still a further embodiment of the present disclosure relates to a composition for preventing, treating, or alleviating a carbonic anhydrase-associated disease, comprising the antibody, the nucleic acid molecule, the vector, and/or the host cell, or use of the antibody, the nucleic acid molecule, the vector, and/or the host cell in preventing, treating, or alleviating a carbonic anhydrase-associated disease.

Still another embodiment of the present disclosure relates to a method for preventing, treating, or alleviating a carbonic anhydrase-associated disease, comprising administering a composition comprising the antibody, the nucleic acid molecule, the vector, and/or the host cell to a subject afflicted with a carbonic anhydrase-associated disease.

Yet a further embodiment of the present disclosure relates to a composition or a method for reducing solid tumors or solid tumor cells in size or for inducing or promoting tumor regression.

Technical Solution

The present disclosure addresses an antibody recognizing and binding to carbonic anhydrase, a nucleic acid molecule coding for the antibody or an antigen-binding fragment, a vector carrying the nucleic acid molecule, a host cell including the nucleic acid molecule or the vector, and use of the antibody or an antigen-binding fragment thereof in the alleviation, prophylaxis, therapy or diagnosis of CA-MI-positive solid tumors.

Useful in the present disclosure is an antibody that specifically recognizes and binds to carbonic anhydrase. In detail, the antibody of the present disclosure binds to CA-XII. The antigen determinant, that is, the epitope to which the antibody of the present disclosure binds, is a non-catalytic region, located at an N terminus of CA-XII. Preferably, the CA-XII is an enzyme derived from a human. Particularly, the human-derived CA-XII has the amino acid sequence of SEQ ID NO: 5.

The term "catalytic domain" is a concept well known in the art, and relates, in conjunction with the present disclosure, to the portion of CA-XII at which the catalysis of carbonic acid to bicarbonate and protons occurs. In contrast, the term "non-catalytic domain" refers to a portion other than the catalytic domain at which the catalysis of carbonic acid to bicarbonate and protons occurs. In the present disclosure, the non-catalytic domain of CA-XII is an N-terminal, non-catalytic domain, and may mean a peptide consisting of 93 amino acid residues from the N-terminal position 1 to position 93 on the amino acid sequence of SEQ ID NO: 5 for the human-derived CA-XII, or a fragment thereof.

The epitope recognized by the antibody of the present disclosure may be a peptide, composed of 7 to 93 consecutive amino acids, containing the amino acid sequence of SEQ ID NO: 1, 2, 3, or 4.

In one embodiment, the epitope recognized by the antibody of the present disclosure may be a peptide composed of 7 to 93 consecutive amino acid residues on the amino acid sequence of SEQ ID NO: 5, essentially containing the amino acid sequence of SEQ ID NO: 1, particularly, a peptide composed of 14 to 93 consecutive amino acid residues on the amino acid sequence of SEQ ID NO: 5, essentially containing the amino acid sequence of SEQ ID NO: 2, more particularly, a peptide composed of 7 to 14 consecutive amino acids on the amino acid sequence of SEQ ID NO: 2, essentially containing the amino acid sequence of SEQ ID NO: 1, and further more particularly, a peptide composed of the amino acid sequence of SEQ ID NO: 1 or 2.

On the amino acid sequence of SEQ ID NO: 5, which is the amino acid sequence of the human-derived CA-XII, the amino acid sequence of SEQ ID NO: 1 corresponds to amino acids in sequence from position 32 to position 38 and the amino acid sequence of SEQ ID NO: 2 corresponds to amino acids in sequence from position 25 to position 38.

According to an embodiment of the present disclosure, the antibody may comprise at least one selected from the group consisting of amino acid sequences of SEQ ID NOS: 6 to 8, each accounting for an individual CDR of the $V_H$ region, and amino acid sequences of SEQ ID NOS: 9 to 11, each corresponds to an individual CDR of the $V_L$ region. In a particular embodiment, the antibody of the present disclosure may comprise amino acid sequences of SEQ ID NOS: 6, 7, and 8, which correspond respectively to CDR1, CDR2, and CDR3 of the $V_H$ region, and/or amino acid sequences of SEQ ID NOS: 9, 10, and 11, which account respectively for CDR1, CDR2, and CDR3 of the $V_L$ region. The antibody according to another embodiment of the present disclosure may comprise the amino acid sequence of SEQ ID NO: 12 and the amino acid sequence of SEQ ID NO: 13, which cover a $V_H$ region and a $V_L$ region, respectively.

In one embodiment of the present disclosure, an antibody binding to a peptide comprising the amino acid sequence of SEQ ID NO: 1 is designated 27B6. According to some embodiments, the antibody may comprise CDRs 1-3 of the heavy chain variable region and CDRs 1-3 of the light chain variable region of the antibody produced by the hybridoma cell of Accession No. KCLRF-BP-00280.

Alternatively, the epitope recognized by the antibody may be a peptide composed of 14 to 93 consecutive amino acid residues on the amino acid sequence of SEQ ID NO: 5, essentially containing the amino acid sequence of SEQ ID NO: 3, particularly, a peptide composed of 19 to 93 consecutive amino acid residues on the amino acid sequence of SEQ ID NO: 5, essentially containing the amino acid sequence of SEQ ID NO: 4, more particularly, a peptide composed of 14 to 19 consecutive amino acids on the amino acid sequence of SEQ ID NO: 4, essentially containing the amino acid sequence of SEQ ID NO: 3, and further more particularly, a peptide composed of the amino acid sequence of SEQ ID NO: 3 or 4.

On the amino acid sequence of SEQ ID NO: 5, which is the amino acid sequence of the human-derived CA-XII, the amino acid sequence of SEQ ID NO: 3 corresponds to amino acids in sequence from position 39 to position 52 and the amino acid sequence of SEQ ID NO: 4 corresponds to amino acids in sequence from position 39 to position 57.

According to an embodiment of the present disclosure, the antibody may comprise at least one selected from the group consisting of amino acid sequences of SEQ ID NOS: 14 to 16, each accounting for an individual CDR of the $V_H$ region, and amino acid sequences of SEQ ID NOS: 17 to 19, each accounting for an individual CDR of the $V_L$ region. In a particular embodiment, the antibody of the present disclosure may comprise amino acid sequences of SEQ ID NOS: 14, 15, and 16, which account respectively for CDR1, CDR2, and CDR3 of the $V_H$ region, and/or amino acid sequences of SEQ ID NOS: 16, 17, and 18, which account respectively for CDR1, CDR2, and CDR3 of the $V_L$ region. The antibody according to another embodiment of the present disclosure may comprise the amino acid sequence of SEQ ID NO: 20 and the amino acid sequence of SEQ ID NO: 21, which cover a $V_H$ region and a $V_L$ region, respectively.

In one embodiment of the present disclosure, an antibody binding to a peptide comprising the amino acid sequence of SEQ ID NO: 3 is designated 4B4. According to some embodiments, the antibody may comprise CDRs 1-3 of the heavy chain variable region and CDRs 1-3 of the light chain variable region of the antibody produced by the hybridoma cell of Accession No. KCLRF-BP-00279.

The antibodies 26B6 and 4B4 according to some embodiments of the present disclosure can bind, together, to the same antigen because their epitopes do not overlap. Hence, the two antibodies may be useful in a sandwich ELISA assay for the CA-XII antigen. In sandwich ELISA, particularly, the 27B6 antibody may be used as a capture antibody while the 4B4 antibody may be used as a detector antibody.

The antibody or the antigen-binding fragment thereof in accordance with an embodiment of the present disclosure exhibits tumor regression activity and a direct inhibitory effect on tumor cell lines. As used herein, the term "tumor regression" is intended to encompass the induction or promotion of the decrease of tumor size, and/or the inhibition, interruption, or reduction of tumor cell growth. The decrease of tumor size means that, when the antibody or a fragment thereof according to the present disclosure is administered, a tumor decreases in size to, for example, 97% or less, 95% or less, 90% or less, 85% or less, 80% or less, or 75% or less of the size of the tumor before administration.

The antibody according to the present disclosure exhibits both antibody-dependent cell-mediated cytotoxicity (ADCC) and complement-dependent cytotoxicity (CDC).

According to the present disclosure, the antibody may be defucosylated, either partially or completely. The defucosylated antibody according to the present disclosure retains the activity of inhibiting the growth of solid tumors and promoting tumor regression. For example, the 27B6 antibody exhibits a higher suppressive effect on breast cancer when it is fucosylated than when it is defucosylated. On the other hand, the 4B4 antibody in a defucosylated form is superior in anti-tumor effect to that in a fucosylated form (FIGS. 22 and 23).

The antibody or antigen-binding fragment thereof according to the present disclosure may not exist in the body or may be a non-naturally occurring substance. In this case, the antibody or antigen-binding fragment thereof may be recombinant or synthetic. Recombinant or synthetic antibodies or antigen-binding fragments thereof can be produced using techniques well known in the art.

Also, contemplated in accordance with another embodiment of the present disclosure is a substance recognizing an antigen-determining region of CA-XII. The substance may be selected from the group consisting of an antibody, an antibody fragment, and a ligand. The antibody may be polyclonal or monoclonal, and may be derived from humans or animals. For example, the antibody may be monoclonal. Monoclonal antibodies may be prepared using a method known in the art, for example, a phage display technique. A mouse antibody and a chimeric antibody fall within the scope of the antibody according to the present disclosure.

The term "CDR (Complementarity Determining Region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope.

Throughout the specification, the terms “specifically binding” or “specifically recognizing” has the same meaning as is generally known to a person of ordinary skill in the art, indicating that an antigen and an antibody specifically interact with each other to cause an immunological response.

The term “antigen-binding fragment,” means a fragment of the full structure of an immunoglobulin, which is a partial polypeptide including a domain to which an antigen can bind. For example, it may be scFv, $(scFv)_2$, scFv-Fc, Fab, Fab', or $F(ab')_2$, but is not limited thereto.

The anti-CA-XII antibody or fragment thereof may be coupled to various labeling agents, toxins, or anti-tumor drugs. It will be apparent to those skilled in the art that the antibody of the invention can be coupled to a labeling agent, a toxin, or an anti-tumor drug by a method well known in the art. Such coupling may be chemically conducted on the site of attachment after expression of the antibody or antigen. Alternatively, the coupling product may be engineered into the antibody or antigen of the invention at the DNA level. Subsequently, the DNA is then expressed in a suitable host system as described herein below, and the expressed proteins are collected and, if necessary, renatured. Coupling may be achieved via a linker, known in the art. In particular, different linkers that release a toxin or an anti-tumor drug under acidic or alkaline conditions or upon exposure to specific proteases may be employed with this technology.

In some embodiments, it may be desirable for the labeling agent, toxin, or anti-tumor drug to be attached to spacer arms of various lengths to reduce potential steric hindrance.

In this context, the labeling agent may be selected from the group consisting of a radioisotope, a hapten or a fluorescent, a chromogen, and a dye. By way of example, the labeling agent may be selected from among FLAG, GFP, YFP, RFP, dTomato, cherry, Cy3, Cy5, Cy5.5., Cy7, DNP, AMCA, biotin, digoxigenin, Tamra, Texas Red, rhodamine, Alexa fluors, FITC, and TRITC. Alternatively, the labeling agent may be a radioisotope such as, for example, $^{3}H$, $^{14}C$, $^{15}N$, $^{35}S$, $^{90}Y$, $^{99}Tc$, $^{111}In$, $^{125}I$, or $^{131}I$. Further examples of a suitable labeling agent include enzymatic groups (e.g. horseradish peroxidase, horseradish galactosidase, luciferase, alkaline phosphatase), chemiluminescent groups, biotinyl groups, or predetermined polypeptide epitopes recognized by a secondary reporter.

So long as it is toxic to cells or organisms, any toxin may be used in the present disclosure. To quote an example, a radioisotope, a small molecule, a peptide, or a protein may be used as a toxin. The antibody or fragment thereof may be coupled with a toxin to form a fusion protein. As a proteinous toxin, ricin, saporin, gelonin, momordin, diphtheria toxin, or pseudomonas toxin may be used. As for the radioisotope, its examples include $^{131}I$, $^{188}Rh$, and $^{90}Y$, but are not limited thereto.

As used herein, the term “anti-tumor drug” specifies a drug capable of either stopping or slowing down the abnormal growth of tissues. Thus, anti-tumor drugs are particularly useful in treating cancer. An anti-tumor drug may be an angiogenesis inhibitor, a DNA intercalator or a DNA cross-linker, a DNA synthesis inhibitor, a DNA-RNA transcription regulator, an enzyme inhibitor, a gene regulator, a microtubule inhibitor, or other antitumor agents.

The present disclosure further addresses a nucleic acid molecule encoding the antibody of the present disclosure. The nucleic acid molecule of the present disclosure, encoding the antibody of the present disclosure, may be, for example, a DNA, a cDNA, an RNA, a synthetically produced DNA or RNA, or a recombinantly produced chimeric nucleic acid molecule comprising any of those nucleic acid molecules, either alone or in combination. The nucleic acid molecule may also be genomic DNA corresponding to an entire gene or a substantial portion thereof, or to a fragment or derivative thereof. The nucleotide sequence of the nucleic acid molecule may be a modified nucleotide sequence in which substitution, deletion or addition occurs on one or more nucleotide residues, thus achieving substitution or mutation of at least one amino acid residue of the amino acid sequence of the antibody. In a particular embodiment of the present disclosure, the nucleic acid molecule is a cDNA molecule.

One embodiment of the present disclosure also relates to a vector comprising the nucleic acid molecule in an expressible form. The vector of the present disclosure may be, for example, a phage, a plasmid, a viral vector, or a retroviral vector. Retroviral vectors may be replication-competent or replication-defective. In the latter case, viral propagation will generally occur in complementing host/cells.

The aforementioned nucleic acid molecule may be inserted into a vector such that translational fusion with another polynucleotide occurs. Generally, a vector may contain one or more origins of replication (ori) and inheritance systems for cloning or expression, one or more markers for selection in the host, e.g., antibiotic resistance, and one or more expression cassettes. Examples of a suitable origin of replication (ori) include the Col E1, the SV40 viral and the M 13 origins of replication.

In the present disclosure, the nucleic acid molecule may be designed for introduction into a host, either directly or via a liposome, a phage vector, or a viral vector (e.g. adenoviral vector, retroviral vector, etc.). Additionally, baculoviral systems, or systems based on vaccinia virus or semliki forest virus can be used as eukaryotic expression systems for the nucleic acid molecules of the present disclosure.

Another embodiment of the present disclosure pertains to a non-human host including the vector of the present disclosure. The host may be prokaryotic or eukaryotic. The polynucleotide or vector of the present disclosure, present in a host cell, may either be integrated into the genome of the host cell or may be maintained extrachromosomally.

In addition, the present disclosure is concerned with a transgenic, non-human animal, available for the production of the antibody of the present disclosure, comprising one or more nucleic acid molecules of the present disclosure. Antibodies can be produced in and recovered from tissue or body fluids, such as milk, blood or urine, from goats, cows, horses, pigs, rats, mice, rabbits, hamsters or other mammals.

Moreover, the present disclosure provides a method for producing a substance selectively recognizing an antigen-determining region of CA-XII. Also, the present disclosure provides a cell line producing an antibody selectively recognizing an antigen-determining region of CA-XII. An antibody to an antigen-determining region of CA-XII, or a fragment thereof, may be produced using a typical method with a CA-XII protein, an antigen-determining region of CA-XII, a portion of CA-XII containing an antigen-determining region of CA-XII, or a cell expressing an antigen-determining region of CA-XII serving as an antigen. For example, a method for producing an anti-CA-XII antibody can be achieved through a method for producing a cell line producing an anti-CA-XII antibody, comprising (a) injecting and immunizing an animal with a CA-XII protein, an antigen-determining region of CA-XII, a portion of CA-XII containing an antigen-determining region of CA-XII, or a cell expressing an antigen-determining region of CA-XII, (b) obtaining splenocytes producing an antibody specific for CA-XII, and (c) fusing the splenocytes with myeloma cells to give hybridoma cells and selecting a hybridoma cell producing an antibody to CA-XII. The antibody can be isolated by culturing the cell line in vitro or by introducing the cell line in vivo. For example, the cell line may be intraperitoneally injected into mice, followed by isolating and purifying the antibody from the ascites. Isolation and purification of monoclonal antibodies may be achieved by subjecting the culture supernatant and ascites to ion exchange chromatography (DEAE or DE52) or affinity chromatography using an anti-immunoglobulin column or protein A column.

The antigen-determining region to which the antibody of the present disclosure binds exhibits solid tumor-specific expression. Hence, the anti-CA-XII antibody can not only be effectively used to detect tumor cells, but can also exert cytotoxicity only on tumor cells when it carries a toxic substance.

A further embodiment of the present disclosure provides the use of CA-XII, particularly an antigen-determining region, located at a non-catalytic domain, of CA-XII, in detecting solid tumors. Also, provided is a composition for detecting cancer stem cells of solid tumors, comprising a substance interacting with the antigen-determining region. The interacting substance may be any substance that is able to interact with CA-XII, particularly an antigen-determining region of CD-XII, located at a non-catalytic domain thereof. In particular, the interacting substance may be selected from the group consisting of a small molecular chemical, an antibody, an antigen-binding fragment of an antibody, an aptamer, or a combination thereof.

In another embodiment, the present disclosure relates to a diagnostic composition, comprising the antibody of the present disclosure, the nucleic acid molecule of the present disclosure, the vector of the present disclosure, or the host of the present disclosure. The term "diagnostic composition", as used herein, refers to a composition comprising at least one of the antibody, the nucleic acid molecule, the vector, and/or the host of the present disclosure.

The diagnostic composition of the invention is useful in the detection of undesired expression or over-expression of CA, in particular, CA-XII, in different cells, tissues or another suitable sample, by contacting a sample with an antibody of the present disclosure and determining the presence of a CA, in particular CA-XII, in the sample. Accordingly, the diagnostic composition of the invention may be available for assessing the onset or status of disease, as defined herein below. In particular, malignant cells, such as cancer cells, expressive of CA, in particular CA-XII, can be targeted with the antibody of the present disclosure, or a fragment or derivative thereof. The cells which have bound the antibody of the present disclosure might thus be attacked by immune system functions such as the complement system or by cell-mediated cytotoxicity, therefore reducing the number of, or completely eradicating, cells showing undesired expression or over-expression of CA, in particular CA-XII.

In another embodiment, the antibody of the present disclosure, or a fragment or derivative thereof, is coupled to a labeling agent. Such antibodies are particularly suitable for diagnostic applications.

The diagnostic composition of the invention can be administered as an active agent alone or in combination with other agents.

A still further embodiment of the present disclosure addresses a method for screening a tumor cell. The method comprises (a) reacting the anti-CA-XII antibody with a sample including a tumor cell, and (b) determining that the sample is a tumor if the sample is positive to the antibody. The sample may include, but is not limited to, lymphoid fluid, bone marrow, blood, and blood corpuscles. The tumor cell may preferably be a breast cancer cell, a lung cancer cell, a stomach cancer cell, a prostate cancer cell, or a liver cancer cell.

When used for screening a tumor cell, the anti-CA-XII antibody may be conjugated with a label capable of indicating antigen-antibody reactivity. The label useful for this purpose may include a radioisotope, a fluorescent, a luminescent, a chromogen, and a dye.

Also, the anti-CA-XII antibody of the present disclosure may be provided for a kit for diagnosing solid tumors.

The term "solid tumor" in accordance with the invention defines an abnormal mass of tissue that usually does not contain cysts or liquid areas. Solid tumors may be benign (not cancer), or malignant (often referred to in the art as cancer). Examples of the solid tumor to which the antibody of the present disclosure is applicable include stomach cancer, breast cancer, lung cancer, colorectal cancer, liver cancer, gallbladder cancer, liver cancer, pancreatic cancer, thyroid cancer, prostate cancer, ovarian cancer, uterine cervical cancer, bladder cancer, sarcoma, glioma, cancerous tumors, mesothelioma, lymphoma, colorectal tumors, hepatic tumors, prostate tumors, pancreatic tumors, and head and neck tumors, with preference for breast cancer, lung cancer, colorectal cancer, stomach cancer, prostate cancer, and liver cancer. Here, breast cancer may preferably be triple-negative breast cancer (TNBC), which does not express the genes for HER2, estrogen receptor (ER), and progesterone receptor (PR), which makes it difficult to detect triple-negative breast cancer.

The diagnostic kit may comprise a means for detecting an antigen-antibody reaction in addition to the anti-CA-XII antibody. The detecting means may be an agent useful for performing a technique selected from the group consisting of flow cytometry, immunohistochemical staining, enzyme-linked immunosorbent assay (ELISA), radioimmunoassay (RIA), enzyme immunoassay (EIA), fluorescence immunoassay (HA), and luminescence immunoassay (LIA). In this context, the label may be an enzyme such as HRP (horse radish peroxidase), a fluorescent such as FITC (fluorescein-thiocarbamyl ethylenediamine), a luminescent such as luminol, isoluminol, and lucigenin, or a radioisotope such as $^{125}I$, $^{3}H$, $^{14}C$, and $^{131}I$, but is not limited thereto. Conjugation with a label can be determined using a means for measuring an enzymatic reaction with a substrate, fluorescence, luminescence, or radiation. For example, the anti-CA-XII antibody may be prepared for use in an ELISA kit or a strip kit.

The antibodies 27B6 and 4B4 according to some embodiments of the present disclosure can bind, together, to the same antigen because their epitopes do not overlap. Accordingly, the two antibodies may be useful in a sandwich ELISA assay for CA-XII antigen. In sandwich ELISA, particularly, the 27B6 antibody may be used as a capture antibody while the 4B4 antibody may serve as a detector antibody.

In accordance with an embodiment thereof, the present disclosure addresses a pharmaceutical composition comprising the antibody, the nucleic acid molecule, the vector, or the host of the present disclosure. The antibody, the nucleic acid molecule, the vector, or the host of the present disclosure is used for treating or regressing solid cancer. The treatment or regression of solid tumors can be achieved by administering the nucleic acid molecule, the vector, or the host of the present disclosure at an effective dose to a subject in need thereof.

The term "solid tumor", as used herein, defines an abnormal mass of tissue that usually does not contain cysts or liquid areas. The solid tumor may be benign (not cancer) or malignant (often referred to in the art as cancer). Examples of the solid tumor to which the antibody of the present disclosure is applicable include stomach cancer, breast cancer, lung cancer, colorectal cancer, liver cancer, gallbladder cancer, liver cancer, pancreatic cancer, thyroid cancer, prostate cancer, ovarian cancer, uterine cervical cancer, bladder cancer, sarcoma, glioma, cancerous tumors, mesothelioma, lymphoma, colorectal tumors, hepatic tumors, prostate tumors, pancreatic tumors, and head and neck tumors, with preference for breast cancer, lung cancer, colorectal cancer, stomach cancer, prostate cancer, and liver cancer. The breast cancer may preferably be triple-negative breast cancer (TNBC), which does not express the genes for HER2, estrogen receptor (ER), or progesterone receptor (PR), which makes it difficult to detect triple-negative breast cancer.

The therapeutic effect of solid tumors in accordance with the present disclosure includes suppressing effects on the migration, invasion, and metastasis of cancer cells (particularly, cancer stem cells) or tissues including tumor cells, and thus on the malignancy of cancer as well as their growth inhibition (quantitative reduction) and apoptosis.

As used herein the term "subject" or "patient" refers to a mammal, including a primate such as a human, a monkey, etc., and a rodent such as a mouse, a rat, etc., that is afflicted with, or has the potential to be afflicted with a solid tumor or symptom and thus which is in need of alleviation, prevention, and/or treatment of the solid tumor.

The administration of the antibody or its fragment according to the present disclosure may be conducted in any acceptable manner. For example, a therapeutic agent including the anti-CA-XII antibody as an active ingredient is administered orally or parenterally, and preferably parenterally, to a subject, e.g., a human or an animal that has tumor cells. The therapeutic agent may include a pharmaceutically acceptable excipient, and the dose of the therapeutic agent may vary depending on the condition of the patient, and may range from, for example, 3 mg to 6,000 mg per day. The therapeutic agent may take such forms as liquids, powders, emulsions, suspensions or injections, but is not limited thereto.

Further, the present disclosure provides a method for treating acute or chronic myelogenous or lymphocytic leukemia, using at least one selected from among an antibody to an antigen-determining region of CA-XII, a fragment of the antibody ($F(ab')_2$, Fab, Fv, etc.), and a ligand to an antigen-determining region of CA-XII.

An antibody or a fragment thereof may be monoclonal or polyclonal, and may be derived from humans or animals. The anti-CA-XII antibody or its fragment may further comprise the toxin described above. The toxin may be fused, coupled, conjugated or linked to the antibody using a well-known technique.

The pharmaceutical composition of the present disclosure may be administered as a single active agent or in combination with any other agents that are preferable for the treatment of the disease of interest. In addition, the antibody of the present disclosure may be used in conjunction with other anticancer therapies, such as chemotherapy, radiotherapy, cytotherapy, etc. Various, well-known anticancer agents may be used in chemotherapy or cytotherapy.

Another embodiment of the present disclosure provides a method for screening a therapeutic agent or inhibitor of solid tumors, comprising contacting a candidate compound with CA-XII, particularly an antigen-determining region located at a non-catalytic domain of CA-XII, and classifying the candidate compound as a potential therapeutic agent for solid tumors if the candidate compound is determined to bind to the antigen-determining region. A further embodiment of the present disclosure provides a pharmaceutical composition for treating solid tumors, comprising the screened therapeutic agent for solid tumors as an active ingredient.

The candidate compound may be at least one selected from the group consisting of various synthetic or naturally occurring compounds, polypeptides, oligopeptides, peptides or protein constructs (e.g., antibodies, antigen-binding fragments, peptibodies, nanobodies, etc.), polynucleotides, oligonucleotides, antisense-RNA, shRNA (short hairpin RNA), siRNA (small interference RNA), aptamers, and extracts from natural products.

Binding between a candidate compound and an antigen-determining region can be determining by detecting the formation of a complex, which can be conducted using various methods known in the art. By way of example, typical enzyme reactions, fluorescence, luminescence and/or radiation may be detected to confirm the binding of the candidate compound to the antigen-binding region. In detail, techniques available for the detection of the complex include, but are not limited to, immunochromatography, immunohistochemistry, enzyme-linked immunosorbent assays (ELISA), radioimmunoassays (RIA), enzyme immunoassays (EIA), fluorescence immunoassays (FIA), luminescence immunoassays (LIA), and Western blotting.

Advantageous Effects

Provided are an antibody recognizing and binding to carbonic anhydrase, a nucleic acid molecule encoding the antibody or an antigen-binding fragment of the antibody, a vector carrying the nucleic acid molecule, a host cell including the vector or the nucleic acid molecule, and use of the antibody or an antigen-binding fragment thereof in the alleviation, prevention or diagnosis of solid tumors.

DESCRIPTION OF DRAWINGS

FIG. 1 shows titers of the solid tumor-specific 27B6 monoclonal antibody in peripheral blood, as measured according to Example 1.

FIG. 2 shows variable region sequences including CDR sequences of the 27B6 and 4B4 antibodies, as determined according to Example 2, FIG. 3 shows the antigen specificity and affinity of the 27B6 chimeric antibody, as measured according to Example 3;

FIG. 4 illustrates a procedure of screening titers of the 4B4 monoclonal antibody in peripheral blood, as measured according to Example 4, FIG. 5 shows the antigen specificity and affinity of the 4B4 chimeric antibody, as measured according to Example 5;

FIGS. 6*a*, 6*b* and 6*c* show expression patterns of the carbonic anhydrase 12 antigen in various breast cancer cells, as measured according to Example 6, FIG. 7 shows electrophoretograms of antigens isolated and purified from the lung adenocarcinomic A549 cell line through columns fabricated with 4B4 and 27B6 monoclonal antibodies;

FIG. 8 lists proteins identified by LC-MS/MS analysis from purified antigens, as analyzed according to Example 7, FIG. 9 shows the amino acid sequence of carbonic anhydrase 12 isoform 1 in which amino acid sequences of the antigens for 4B4 and 27B6 antibodies, detected by LC-MS/MS, are marked, as analyzed according to Example 7, FIG. 10 shows the identification of carbonic anhydrase 12 as an antigen for the 4B4 and the 27B6 monoclonal antibody, as analyzed by ELISA assay in Example 7, FIG. 11 shows the identification of carbonic anhydrase 12 as an antigen for the 4B4 and the 27B6 monoclonal antibody, as analyzed by Western blotting assay in Example 7, FIG. 12 shows the concurrent recognition of carbonic anhydrase 12 by 4B4 and 27B6 monoclonal antibodies as measured by sandwich ELISA assay using 4B4 and 27B6 monoclonal antibodies as capture/detector antibodies in Example 7, FIG. 13 shows epitope mapping processes and results of 27B6 and 4B4 monoclonal antibodies, as analyzed according to Example 8, FIG. 14 shows the complement-dependent cytotoxic effects of 27B6 and 4B4 antibodies, as analyzed according to Example 9, FIG. 15 shows the complement-dependent cytotoxic effects of the 27B6 antibody in triple-negative breast cancer, as analyzed according to Example 9, FIG. 16 shows antibody-dependent cell-mediated cytotoxic effects of the 27B6 antibody, as analyzed according to Example 10-1, FIG. 17 shows antibody-dependent cell-mediated cytotoxic effects of the 27B6 antibody on triple-negative breast cancer cell lines, as analyzed according to Example 10-2, FIG. 18 shows the antibody-dependent cell-mediated cytotoxic effects of the defucosylated 27B6 chimeric antibody, as analyzed according to Example 11-1, FIG. 19 shows the antibody-dependent cell-mediated cytotoxic effects of the defucosylated 4B4 and 27B6 chimeric antibodies, as analyzed by a luciferase assay in Example 11-2.

FIG. 20 shows the expression levels of the CA12 antigen on triple-negative breast cancer cell lines and the binding of 27B6 and 4B4 antibodies to the cell surface of the cell lines, as analyzed according to Example 12.

FIG. 21 shows the inhibitory activities of 27B6 and 4B4 antibodies against tumor growth in triple-negative breast cancer animal models.

FIG. 22 shows the inhibitory activity of the 27B6 antibody against triple-negative breast cancer, as analyzed according to Example 12.

FIG. 23 shows the inhibitory activity of the 4B4 antibody against triple-negative breast cancer, as analyzed according to Example 12.

FIGS. 24 and 25 show that the binding of the 4B4 antibody alone to tumor cells does not affect the growth of the tumor cells.

FIG. 26 shows the effect of a combination of the 27B6 antibody and radiotherapy, as analyzed according to Example 14.

MODE FOR INVENTION

A better understanding of the present invention may be obtained through the following examples which are set forth to illustrate, but are not to be construed as limiting the present invention.

EXAMPLE 1

Production of 27B6 Monoclonal Antibody

The development of novel antibodies specific for CA12 was achieved in the following experiments. The developed antibodies were observed to be specific for solid tumors, such as adenocarcinoma of the lungs, breast cancer, colorectal cancer, and prostate cancer, as they reacted with antigens expressed specifically in the tumors. They were designated 27B6 and 4B4, respectively.

1-1: Design of Target Site for Construction of 27B6 Monoclonal Antibody

An antibody specific for solid tumor cells was fabricated. For this, mice were immunized directly with solid tumor cells, and monoclonal antibodies were established using a cell fusion technique. Thereafter, an antigen to which the solid tumor cell-specific monoclonal antibody was bound was analyzed and identified.

1-2: Preparation of Hybridoma Cell

In order to develop a monoclonal antibody to an antigen specifically expressed in solid tumors, A549 cells, which are adenocarcinomic human alveolar-basal epithelial cells, were immunized, and a selection was made of an antibody that was positive to the A549 cell line, but negative to the normal cell line L132 during a hybridoma selection process.

To the end, Balb/c female mice 6 weeks old were each IP (intraperitoneal cavity)-injected with the A549 cell line (ATCC CCL-185) at a dose of $1\times10^7$ cells three times at regular intervals of three weeks, followed by removing sera from the veins. A dilution of the serum was added to A549 cells. After being left for 30 min at 4° C. to react, the dilution was mixed with 3 ml of PBS and centrifuged for 3 min at 1500 rpm. Unbound antibodies were washed off. A 200-fold dilution of the secondary antibody goat anti-mouse Ig-FITC (Dinona) was used to detect the bound antibodies. After reaction for 15 min at 4° C., the reaction mixture was washed with 3 ml of PBS in the same manner. The sera were measured for antibody titer to A549 cells by flow cytometry. The sera immunized with A549 cells were observed to be highly positive to A549 cells (results not shown). Briefly, three days before a cell fusion experiment, 50 μg of anti-CD40 agonist mAb was added to boost an immune reaction, and A549 (ATCC CCL-185) was injected at a dose of $1\times10^7$ cells to induce the amplification of an antibody to a surface antigen of A549.

1-3: Preparation of Hybridoma Cell

The spleen was excised from the immunized mice, and a suspension of single splenocytes was obtained and washed twice with RPMI (GIBCO). Viable cells were counted using a 1:1 (v/v) mixture of 0.4% trypan blue (Sigma), which stains only dead cells. The X63 mouse myeloma cell line (ATCC CRL-1580) was employed as a cell fusion partner, and washed and counted in the same manner as the splenocytes.

The myeloma cells were mixed at a ratio of 1:5 with the splenocytes and centrifuged. The pellet thus obtained was slowly added over 1 min with 1 ml of 50% PEG (polyethylene glycol) 1500 preheated to 37° C. After being incubated for about 1 min, the cell mixture was slowly diluted with an RPMI medium and centrifuged. The resulting cell pellet was resuspended in RPMI (20% PBS) containing 1×HAT (hypoxanthine-aminopterin-thymidine), plated at a volume of 150 μl/well into 96-well plates, and grown in a 37° C. $CO_2$ incubator. HAT was fed over a predetermined time after the fusion. When a colony was observed in the wells, 150 μl of an HT medium was added to each well, followed by incubation for 48 hrs in a 37° C., 5% $CO_2$ incubator. Then, three-color immunofluorescence staining was performed before flow cytometry. Briefly, the lung adenocarcinoma cell line A549 and the normal lung cell line L132 were immunologically stained with two different dyes and mixed at a ratio of 1:1. This cell mixture was incubated with 100 μl of a supernatant of the hybridoma cell culture at 4° C. for 30 min and centrifuged, together with 3 ml of PBS, at 1500 rpm for 3 min to remove unbound antibodies. The bound antibodies were detected by incubation with a 200-fold dilution of the secondary antibody goat anti-Mouse Ig-APC (Dinona) at 4° C. for 15 min, followed by washing with 3 ml of PBS in the same manner. Thereafter, the hybridoma cells were measured via flow cytometry.

An examination was made to see whether the antibody binds to peripheral blood. For this, PBMC (peripheral blood mononuclear cells from the Korean Red Cross Blood Services) was incubated with 100 μl of a hybridoma supernatant at 4° C. for 30 min, and centrifuged, together with 3 ml of PBS, at 1,500 rpm for 3 min to wash off unbound antibodies. A 200-fold dilution of the secondary antibody goat anti-mouse Ig-FITC (Dinona) was used to detect the bound antibodies. After reaction for 15 min at 4° C., the reaction mixture was washed with 3 ml of PBS in the same manner. The antibody titer was measured using flow cytometry, and the results are shown (FIG. 1). FIG. 1 shows titers of the lung adenocarcinoma-specific 27B6 monoclonal antibody in the peripheral blood, as measured via flow cytometry.

In this manner, the antibody that was positive to the lung cancer cell line A549 and negative to the normal lung cell line L132 and all of granulocytes, lymphocytes and monocytes of the peripheral blood were selected and designated "27B6". Finally, during a limiting dilution procedure, 27B6 hybridoma cells were diluted and selected for single colony growth.

The 27B6 hybridoma cell line was deposited on Feb. 14, 2012, with the Korean Cell Line Bank, located at 28, Yongun-Dong, Jongno-Gu, Seoul, Korea, and received Accession No. KCLRF-BP-00280 on Feb. 20, 2012.

EXAMPLE 2

Analysis of 27B6 Monoclonal Antibody 2-1: Determination of Isotype

The 27B6 monoclonal antibody prepared in Example 1 was analyzed for isotype, using a mouse immunoglobulin isotyping ELISA kit (BD Biosciences, USA). Briefly, isotyping was performed with rabbit anti-murine isotype specific antisera (IgG1, IgG2a, IgG2b, IgG3, IgM, IgA, Kappa, Lambda) while peroxidase-labeled goat anti-mouse IgG served as a secondary antibody. Color development was induced with ortho-phenylenediamine (OPD) and a hydrogen peroxide substrate. Absorbance at 450 nm was read.

As a result, the 27B6 monoclonal antibody was identified as mouse IgG1/kappa light chain (results not shown).

2-2: 27B6 Antibody CDR Sequence

An antibody cloning procedure is illustrated in FIG. 2. Heavy and light chain sequences including the CDR sequences of the 27B6 Ab are represented by SEQ ID NOS: 12 and 13, respectively. FIG. 2 shows variable region sequences including CDR sequences of the 27B6 antibody.

TABLE 1

| | | | |
|---|---|---|---|
| b | $V_H$ | QVQLQQSGPQLVWPGASVIK | CDR1: GYSFTNYW |
| | | ISCNTSGYSFTNYWIHWVKQ | CDR2: IDPSDSET |
| | | RPGQGLEWIGMIDPSDSETR | CDR3: TRGIRGGYYAMDY |
| | | LNQKFKDKTTLTVDRSSSTA | |
| | | YMQVSSSTSEDSAVYYCTRG | |
| | | IRGGYYAMDYWGQGTSVTVS | |
| | | S | |
| | $V_L$ | DIQMTQTTSSLSASLGDRVT | CDR1: QDISNY |
| | | ISCRASQDISNYLNWYQQKP | CDR2: YTS |
| | | EGTVKLLIYYTSRLHSGVPS | CDR3: QQGDTLPRT |
| | | RFSGSGSGTDYSLTISNLEQ | |
| | | EDIATYFCQQGDTLPRTFGE | |
| | | GTKLER | |

EXAMPLE 3

Development of 27B6 Chimeric Antibody

When a monoclonal antibody of mouse origin is administered to the human body, the human immune system recognizes the monoclonal antibody as a foreign antigen and thus produces a human anti-mouse antibody (HAMA) to eliminate the mouse antibody from the blood. In addition, the Fc domain of the mouse antibody cannot exert its effective biological functions in the human body. Therefore, not only does the therapeutic effect sharply decrease, but also side effects such as severe allergic reactions and renal dysfunction may be induced. In order to reduce the immunogenicity of the 27B6 antibody upon administration to the human body, a chimeric antibody in which the mouse antibody, except for the variable region, was substituted with the Fc of the human antibody was constructed. The chimeric antibody was observed to be similar in antigen specificity and affinity to the original mouse 27B6 antibody.

To construct a chimeric antibody, the 27B6-HuIgFc DNA prepared in the above-mentioned manner was transfected into the DHFR DG44 cell line derived from CHO cells, followed by a selective culturing procedure in a selective medium to establish a stable cell line producing a 27B6 recombinant antibody. Details are described as follows.

First, three hours before transfection, the DG44 cell line (Invitrogen, Cat No. A1100001) was inoculated at a density of $1\times10^6$ cells/ml into 6-well plates and incubated with 1 ml of GIBCO® CD DG44 Medium (Invitrogen, USA) at 37° C. in a 5% $CO_2$ atmosphere for 3 hrs. Then, the 27B6-HuIgFc DNA prepared in Example 4-1 was transfected into the competent DC 44 cells using an Effectene transfection reagent kit (QIAGEN, Hilden, Germany).

Three days post transfection, the supernatant was taken and added to A549 cells which were then incubated at 4° C. for 30 min. Unbound antibodies were removed by centrifugation, together with 3 ml of PBS, at 1500 rpm for 3 min. The bound antibodies were detected by incubation with a 150-fold dilution of the secondary antibody goat anti-Mouse Ig-FITC (Dinona) at 4° C. for 15 min, followed by washing with 3 ml of PBS in the same manner. Thereafter, the antibody titer to A549 cells was measured using flow cytometry. Subsequently, a stable cell line was established. For this, the medium was exchanged with a PowerCHO medium (LONZA, Switzerland) supplemented with 30 nM MTX (Sigma, USA) and 200 μg/ml G418 (Invitrogen, USA), after which clone selection was started. Concentrations of MTX and G418 in the selection medium were increased with the repetition of clone selection rounds. Each round was set to be three weeks. The final round of clone selection was performed in a PowerCHO medium supplemented with 1000 nM MTX and 400 μg/ml G418. Thereafter, the final cell line was established as a single colony through limiting dilution.

The 27B6 chimeric antibody established in this manner was found to have antigen specificity and affinity to those of the original mouse 27B6 antibody, as measured by flow cytometry (FIG. 3). FIG. 3 shows the antigen specificity and affinity of the 27B6 chimeric antibody.

EXAMPLE 4

Production of 4B4 Antibody 4-1: 27B6 Pairing Antibody

To develop another antibody which recognizes the same antigen but binds to a different epitope, 27B6 pairing antibody was developed.

Firstly to explore the possibility of development of 27B6 paring antibody, sandwich ELIS using chimeric 27B6 and mouse serum was established. In the same manner as in section 1-2, balb/c female mice 6 weeks old were each IP (intraperitoneal cavity)-injected with the A549 cell line (ATCC CCL-185) at a dose of $1\times10^7$ cells three times at regular intervals of three weeks, followed by removing sera from the veins.

The purified 27B6 chimeric antibody was plated at a concentration of 100 ng/well and incubated at 37° C. for 1 hr. The coated plate was then blocked by incubation with 200 μl of a blocking buffer (Sigma) per well at 37° C. for 1 hr. A548 cells were lysed with 1% NP40 lysis buffer at a concentration of $1\times10^7$ cells/ml. The A549 lysate was added at a density of 50 μl/well to the 27B6 coated plate and incubated at 37° C. for 1 hr before three rounds of washing with PBS. To each of the washed wells, 100 μl of a 1,000-fold dilution of the previously obtained serum was added. Following 1 hr of incubation, the wells were washed again with PBS. Finally, the bound antibody was detected with the secondary antibody goat anti-Mouse (Jackson). A 2,000-fold dilution of the secondary antibody was added in an amount of 100 μl to each well, incubated at 37° C., and washed with PBS. Color development was performed by incubation with 50 μl of TMB (3,3',5,5'-tetramethylbenzidine) at room temperature for 10 min in each well. The reaction was stopped with 2N $H_2SO_4$ (Sigma). The antibody titer was measured by reading the absorbance at 450 nm.

As was expected, positive reaction was observed in sandwich ELISA using chimeric 27B6 and mouse serum (data not shown).

4-2: Production of Monoclonal Antibody

Preparation of hybridoma cells from splenocytes of the immunized mice was carried out in the same manner as in Example 1.

The spleen was excised from the immunized mice, and a suspension of single splenocytes was obtained and washed twice with RPMI (GIBCO). Viable cells were counted using a 1:1 (v/v) mixture of 0.4% trypan blue (Sigma), which stains only dead cells. The X63 mouse myeloma cell line (ATCC CRL-1580) was employed as a cell fusion partner, and washed and counted in the same manner as the splenocytes. The myeloma cells were mixed at a ratio of 1:5 with the splenocytes and centrifuged. To the cell pellet thus obtained, 1 ml of 50% PEG (polyethylene glycol) 1500 preheated to 37° C. was slowly added over 1 min. After being incubated for about 1 min, the cell mixture was slowly diluted with an RPMI medium and centrifuged. The resulting cell pellet was resuspended in RPMI (20% FBS) containing 1×HAT (hypoxanthine-aminopterin-thymidine), plated at a volume of 150 μl/well into 96-well plates, and grown in a 37° C. $CO_2$ incubator. HAT was fed over a predetermined time after the fusion. When a colony was observed in the wells, 150 μl of an HT medium was added to each well, followed by incubation for 48 hrs in a 37° C., 5% $CO_2$ incubator. A titer experiment was carried out with 100 μl of the supernatant. As described above, the 27B6 chimeric antibody was plated at a concentration of 100 ng/well and incubated at 37° C. for 1 hr. The coated antibody was then blocked by incubation with 200 μl of a blocking buffer (Sigma) per well at 37° C. for 1 hr. A549 cells were lysed with 1% NP40 lysis buffer at a concentration of $1\times10^7$ cells/ml. The A549 lysate thus obtained was added at a density of 50 μl/well to the coated antibody and incubated at 37° C. for 1 hr before three rounds of washing with PBS. To each of the washed wells, 100 μl of the previously obtained hybridoma supernatant was added. Following 1 hr of incubation, the wells were washed again with PBS.

Finally, the bound antibody was detected with the secondary antibody goat anti-Mouse Ig-HRP (Jackson). A 2,000-fold dilution of the secondary antibody was added in an amount of 100 μl to each well, incubated at 37° C., and washed with PBS. Color development was performed by incubation with 50 μl of TMB (3,3',5,5'-tetramethylbenzidine) at room temperature for 10 min in each well. The reaction was stopped with 2N $H_2SO_4$ (Sigma). The antibody titer was measured by reading the absorbance at 450 nm. In this screening the positive hybridomas were selected and then evaluated with other additional assays as follows.

To evaluate of binding activity to A549 cell surface, the hybridoma supernatants were added to A549 cells. After being left for 30 min at 4° C. to react, the reaction mixture was mixed with 3 ml of PBS and centrifuged for 3 min at 1500 rpm. Unbound antibodies were washed off. A 200-fold dilution of the secondary antibody goat anti-mouse Ig-FITC (Dinona) was used to detect the bound antibodies. After reaction for 15 min at 4° C., the reaction mixture was washed with 3 ml of PBS in the same manner. The antibody binding to A549 cells was measured using flow cytometry.

An examination was made to see whether the antibody binds to peripheral blood. For this, PBMC (peripheral blood mononuclear cells from the Korean Red Cross Blood Services) was incubated with 100 μl of a hybridoma supernatant at 4° C. for 30 min, and centrifuged, together with 3 ml of PBS, at 1,500 rpm for 3 min to wash off unbound antibodies. A 200-fold dilution of the secondary antibody goat anti-mouse Ig-FITC (Dinona) was used to detect the bound antibodies. After reaction for 15 min at 4° C., the reaction mixture was washed with 3 ml of PBS in the same manner. The antibody titer was measured by flow cytometry.

As a result, the antibody that was positive to the lung cancer cell line A549 and negative to the normal lung cell line L132 and to all of the granulocytes, lymphocytes and monocytes in peripheral blood, like 27B6, was selected and designated "4B4". Finally, during a limiting dilution procedure, 4B4 hybridoma cells were diluted and selected for single colony growth (FIG. 4). FIG. 4 shows titers of the 4B4 monoclonal antibody in the peripheral blood, as measured by flow cytometry. The 4B4 hybridoma cell line was deposited on Feb. 14, 2012, with the Korean Cell Line Bank, located at 28, Yongun-Dong, Jongno-Gu, Seoul, Korea, and received Accession No. KCLRF-BP-00279 on Feb. 20, 2012.

4-3: Analysis of 4B4 Antibody

An antibody cloning procedure is illustrated in FIG. 2. Heavy and light chain sequences including the CDR sequences of the 4B4 Ab are represented by SEQ ID NOS: 20 and 21, respectively. FIG. 2 shows variable region sequences including CDR sequences of the 27B6 antibody, with the CDR sequences marked in the variable regions (thickly underlined).

TABLE 2

| | | | |
|---|---|---|---|
| 4B4 Ab | $V_H$ | EIQLQQSGPELVKPGA SVKISCKASGYSYTDY NIYWVRQSQGKSLDWI GYIDPANGDTTYNQKF KGKATLTVDKSSSTAF MHLNSLTSDGSAVYFC ARPIYYGVYWYFDVWG AGTTVTVS | CDR1: GYSYTDYN<br>CDR2: IDPANGDT<br>CDR3: ARPIYYGVYWYFDV |
| | $V_L$ | DIVMTQAAPSVPVTPG ESVSISCRSSKSLLHS NGNTYLYWFLQRPGQS PQLLIYRMSNLASGVP DRFSGSGSGTAFTLRI SRVEAEDVGVYYCMQH LEYPFTFGSGTKLEIK | CDR1: KSLLHSNGNTY,<br>CDR2: RMS<br>CDR3: MQHLEYPFT |

EXAMPLE 5

Development of 4B4 Chimeric Antibody

A cloning procedure of 4B4 antibody is illustrated in FIG. 4.

In order to reduce the immunogenicity of the 4B4 antibody upon administration to the human body, a chimeric antibody in which the mouse antibody, except for the variable region, was substituted with the Fc of the human antibody was constructed. The chimeric antibody was observed to be similar in antigen specificity and affinity to the original mouse 4B4 antibody.

To construct a chimeric antibody, the 4B4-HuIgFc DNA prepared in the above-mentioned manner was transfected into the DHFR DG44 cell line derived from CHO cells, followed by a selective culturing procedure in a selective medium to establish a stable cell line producing a 4B4 recombinant antibody. Details are described as follows.

First, three hours before transfection, the DG44 cell line (Invitrogen, Cat No. A1100001) was inoculated at a density of $1\times10^6$ cells/ml into 6-well plates and incubated with 1 ml of GIBCO® CD DG44 Medium (Invitrogen, USA) at 37° C. in a 5% $CO_2$ atmosphere for 3 hrs. Then, the 4B4-HuIgFc DNA prepared in Example 6-1 was transfected into competent DC 44 cells using an Effectene transfection reagent kit (QIAGEN, Hilden, Germany).

Three days post transfection, the supernatant was taken and added to A549 cells, which were then incubated at 4° C. for 30 min. Unbound antibodies were removed by centrifugation, together with 3 ml of PBS, at 1500 rpm for 3 min. The bound antibodies were detected by incubation with a 150-fold dilution of the secondary antibody goat anti-Mouse C (Dinona) at 4° C. for 15 min, followed by washing with 3 ml of PBS in the same manner. Thereafter, the antibody titer to A549 cells was measured by flow cytometry. Subsequently, a stable cell line was established. For this, the medium was exchanged with a PowerCHO medium (LONZA, Switzerland) supplemented with 30 nM MTX (Sigma, USA) and 200 μg/ml G418 (Invitrogen, USA), after which clone selection was started. Concentrations of MTX and G418 in the selection medium were increased with the repetition of clone selection rounds. Each round was set to be three weeks. The final round of clone selection was performed in a PowerCHO medium supplemented with 1000 nM of MTX and 400 μg/ml of G418. Thereafter, the final cell line was established as a single colony through limiting dilution.

The 4B4 chimeric antibody established in this manner was found to have antigen specificity and affinity similar to those of the original mouse 4B4 antibody, as measured by flow cytometry (FIG. 5). FIG. 5 shows the antigen specificity and affinity of the 4B4 chimeric antibody.

EXAMPLE 6

Analysis of Antibody Expression in Various Cell Lines 6-1: Antibody Expression in Various Cell Lines 27B6 and 4B4 monoclonal antibodies were analyzed for binding to various cell lines obtained from KCLB (Korean Cell Line Bank) and SNU (Seoul National University) using flow cytometry. Briefly, various cell lines were obtained from KCLB (Korean Cell Line Bank) and SNU (Seoul National University). At 37° C. under a 5% $CO_2$ atmosphere, L-132, SW-900, DU145, LNCap, MCF-7, Huh7, and Hs-578T were cultured in Dulbecco's MEM (GIBCO, Invitrogen) supplemented with 10% heat-inactivated fetal bovine serum (FBS; GIBCO, Invitrogen) and A549, NCI-H460, NCI-H417, DLD-1, HCT116, HT-29, SW-480, SW-620, LS174T, PC-3, SNU1, SNU638, SNU719, MKN1, MKN28, MKN45, MKN74, NCI-N87, SK-BR3, MDA-MB231, and MDA-MB453 were cultured in RPMI 1640 (GIBCO, Invitrogen) supplemented with 10% heat-inactivated FBS. In addition, incubation was carried out at 37° C. under a 5% $CO_2$ atmosphere in Eagle's MEM (GIBCO, Invitrogen) supplemented with 10% heat-inactivated fetal bovine serum (FBS; GIBCO, Invitrogen) for Calu-3, Hep3B, SK-HEP-1, C3A, Hep G2, PLC/PRF/5, and BT-20, in IMDM (GIBCO, Invitrogen) supplemented with 20% heat-inactivated fetal bovine serum (FBS; GIBCO, Invitrogen) for KATO III, and in Leibovitz's L-15 medium supplemented with 10% heat-inactivated fetal bovine serum (FBS; GIBCO, Invitrogen) for SW480 and MDA-MB468.

The cultured cancer cell lines were incubated with the 27B6 or the 4B4 monoclonal antibody of the present disclosure at 4° C. for 30 min, washed with PBS, and treated with FITC-conjugated goat anti-mouse IgG (DiNona Inc, Korea) at 4° C. for 15 min. The cell lines were washed again with PBS before analysis by FACScaliber (Becton Dickinson, USA). The results are summarized in Table 3, below. Also, titers of the 27B6 and the 4B4 antibody were measured in various solid tumor cell lines.

As can be seen in Table 3, the 27B6 and the 4B4 monoclonal antibody according to the present disclosure were found to strongly bind to the lung adenocarcinomic cell line A549 and to some of colorectal cancer, stomach cancer, liver cancer, and breast cancer cell lines, but to bind either weakly or not at all to the normal cell line L-132, the small cell carcinoma cell line NCI-H417, 4 colon cancer cell lines including HT-29, 3 prostate cell lines, 7 gastric cell lines, and 5 liver cell lines. The results of PBMC indicate that normal blood cells are negative to both antibodies.

TABLE 3

| Origin | Cell line | 27B6 | 4B4 |
|---|---|---|---|
| Lung | A549 | +++ | +++ |
| | NCl-H460 | ++ | ++ |
| Colon | HCT116 | + | − |
| | HT-29 | + | + |
| | LS174T | +++ | +++ |
| Prostate | LNCap | + | + |
| PBMC | Lymphocyte | − | − |
| | Monocyte | − | − |
| | Granulocyte | − | − |
| Gastric | SNU 719 | + | ++ |
| | MKN 45 | + | +++ |
| Liver | Huh-7 | − | ++ |
| | Hep3B | − | + |
| | PLC/PRF/5 | +++ | +++ |
| Breast | MCF-7 | + | + |
| | SK-BR3 | +++ | +++ |
| | MDAMB231 | +++ | +++ |
| | MDAMB453 | +++ | +++ |
| | BT20 | + | − |

(The percentages of 27B6 and 4B4 positive cells among 5,000 cells were calculated by FACS analysis −: less than 20% of positive cells, +: 20-30%, ++: 40-70%, +++: 60-100%)

6-2: Expression Pattern in Breast Cancer Cell

27B6 and 4B4 were observed to have positive responses to all ER-, PR-, and HER2-positive breast cancer cells. Accordingly, both antibodies can be used as therapeutic agents for various breast cancer subtypes including triple-negative breast cancer.

The binding of the 27B6 and the 4B4 monoclonal antibody to three different phenotype breast cancer cell lines was examined via flow cytometry. Cell culturing was carried out at 37° C. under a 5% $CO_2$ atmosphere for MCF-7 cells in Dulbecco's MEM (GIBCO, Invitrogen) supplemented with 10% heat-inactivated fetal bovine serum (PBS; GIBCO, Invitrogen) and for MDA-MB231 and SK-BR-3 cells in RPMI 1640 (GIBCO, Invitrogen) supplemented with 10% heat-inactivated FBS.

The cultured cancer cell lines were incubated at 4° C. for 30 min with the 27B6 or the 4B4 monoclonal antibody of the present disclosure, washed with PBS, and treated at 4° C. for 15 min with FITC-conjugated goat anti-mouse IgG (DiNona Inc, Korea). The cell lines were washed again with PBS before analysis by FACScaliber (Becton Dickinson, USA). The results are summarized in Table 3.

6-3: IHC (ImmunoHistoChemistry)

Antigens to which 27B6 and 4B4 monoclonal antibodies bind were analyzed for distribution in normal tissues of the human body by immunohistochemistry (IHC). Normal thymus and tonsil tissues of the human body were obtained from the Chungbuk National University Hospital and prepared into cryosections in the department of pathology in the Chungbuk National University Hospital.

The prepared cryosections were subjected to immunohistochemical staining with 27B6 and 4B4 monoclonal antibodies of the present disclosure as follows. Thymus and tonsil cryosections stored at −20° C. or lower were dried at room temperature for 30-60 min, and immersed in 1×PBS for 60 min. Then, the tissues were treated at room temperature for 10 min with 3% $H_2O_2$ to suppress the activity of endogenous peroxidase, washed with flowing water, and blocked at room temperature for 30 min with a goat immunoglobulin-containing serum to exclude non-specific staining with mouse antibodies. Then, the tissues were incubated at room temperature for 60 min with the primary antibody (27B6, 4B4). Each antibody was used at a concentration of 10 μg/ml. Thereafter, the tissues were washed three times with 1×PBS for 5 min, incubated at room temperature for 30 min with an HRP-conjugated goat anti-mouse antibody (Dako, Denmark), and then washed three times with 1×PBST (0.05% Tween20, 1× PBS) for 5 min. The color was developed with diaminobenzidine (DAB), followed by washing for 5 min with flowing water. The tissues were counterstained with hematoxylin and then washed for 7 min with flowing water. After staining, the slides were dehydrated and sealed. The staining results were analyzed by microscopy and are shown in Table 4, below.

As shown in Table 4, the antigens that the 27B6 and the 4B4 monoclonal antibody of the present disclosure recognize are distributed neither in normal thymus nor in normal tonsil tissues. Particularly, nowhere are the antigens expressed in normal mature or immature T cells or B cells. The 27B6 antibody was weakly stained in the basal layer of the tonsil, which, however, seemed to result from non-specific binding.

TABLE 4

| | | 27B6 | 4B4 |
|---|---|---|---|
| Thymus | Cortex | − | − |
| | Medulla | − | − |
| Tonsil | Inter follicular T cell | − | − |
| | B cell | − | − |
| | Germinal center | − | − |
| | | Basal layer + | |

EXAMPLE 7

Analysis of Antigen for Monoclonal Antibody 7-1: Isolation and Purification of 4B4 and 27B6 Monoclonal Antibodies The lung adenocarcinomic cell line A549 that had been used to develop the 4B4 and the 27B6 monoclonal antibody was cultured. Then, $1\times10^8$ cells were suspended in 50 ml of a lysis buffer (1% Nonidet P-40; NP-40 in 50 mM Tris-HCl, pH 7.4, 50 mM EDTA, and 1 mM phenyl-methyl-sulfonyl-fluoride; PMSF) and lysed for 15 min. After centrifugation, the cell debris was removed, and a cell lysate was obtained as a supernatant. The cell lysates was used to separate antigens that were recognized by 4B4 or 27B6 antibodies.

Five mg of each of purified 4B4 and 27B6 monoclonal antibodies were dialyzed against a binding buffer (0.2 M sodium bicarbonate, 0.5M sodium chloride, pH 8.3) to afford two different antibody solutions. A 5-ml column packed with 2 ml of NHS-activated sepharose 4 Fast Flow resin (GE Healthcare) was washed with 20 ml of 1 mM HCl and then with 20 ml of a binding buffer (20 mM sodium bicarbonate, 0.5 M sodium chloride, pH 8.3) so as to allow the prepared antibodies to bind to the column. The column was blocked at the outlet thereof, loaded with either of the two different antibody solutions, and blocked at the inlet thereof. Incubation was performed at room temperature for 4 hrs. Then, 20 ml of a washing buffer (20 mM Sodium acetate, 0.5M sodium chloride, pH 5.4) was made to flow through the column so as to remove excess antibodies that were not bound to the resin. Again, the column was washed with 50 ml of a blocking buffer (0.1 M ethanolamine, 0.5 M sodium chloride, pH 8.3) to remove remaining reaction groups. The two columns were washed with 20 ml of a stock buffer (20 mM Tris-HCl, 150 mM NaCl, 0.02% sodium azide, pH 8.0), and refrigerated until use.

The prepared columns were applied to FPLC (Acta FPLC) so that the antibodies bound to the resin could recognize antigens and thus could allow for the separation of the antigens. The lung adenocarcinomic A549 cell line lysates was loaded to the column coupled to FPLC and used as an antigenic source that was recognized by 4B4 and 27B6 monoclonal antibodies. Antigen separation was performed in a four-step process: equilibrium; sample loading; washing and second washing; elution. An equilibrium buffer and a wash buffer have the same composition: 0.5% Tween-80, 20 mM Sodium phosphate, 150 mM sodium chloride, pH 7.4. This buffer was used in an amount of 10 ml for equilibrium and in an amount of 20 ml for washing. An elution buffer contained 0.3 M Glycine, 0.1 M sucrose, 0.1 M Mannitol, 1.0 M urea, and 0.5% Tween-80, had a pH of 3.0, and was used in an amount of 20 ml for washing. For the second washing, a mixture in which the elution buffer was mixed at a ratio of 25% with the washing buffer was employed. 5 ml of TCA was added to 20 ml of the eluted solution obtained during the antigen separation and stored for 30 min in a refrigerator. After centrifugation, the pellet was further washed twice with acetone. The finally obtained pellet was suspended in 1×SDS-PAGE sample buffer, subjected to electrophoresis, and stained with Coomassie blue. As described above, antigens that were isolated and purified through the columns respectively fabricated with 4B4 and 27B6 antibodies are shown in FIG. 7. FIG. 7 shows electrophoretograms of antigens isolated and purified from the lung adenocarcinomic A549 cell line through columns fabricated with 4B4 and 27B6 monoclonal antibodies.

7-2: Identification of Antigen for 4B4 and 27B6 Monoclonal Antibodies

The antigens isolated and purified from the resin coupled with the 4B4 and the 27B6 monoclonal antibody were visualized as shown in FIG. 7. The two main protein bands indicated by the arrows at about 58 kDa were analyzed in Seoul Pharma Laboratories. For identification, peptides were prepared via in-gel digestion and analyzed using LC-MS/MS, followed by processing the MS/MS spectra with PLGS (Waters) and MASCOT (Matrix Science). A series of analyses was conducted as follows.

Gel pieces containing proteins were dehydrated using 100% CAN (acetonitrile) and completely dried in a Speed-vac. The proteins in the dried gel pieces were digested for 15 min with trypsin. The tryptic peptides were extracted with 60% CAN and 0.1% TFA. The pooled extracts were dried in a Speed-vac. The samples were dissolved in 5% CAN, 0.2% TFA (Trifluoroacetic acid) 20 μl prior to LC-MS/MS analysis. Peptides were eluted from the LC column nanoACQUITY UPLC BEH C18 (1.7 nm, 300 Å, 2.1 mm×150 mm I.D.), with a gradient of a mobile phase buffer A (0.1% TFA in 100% DW) to a mobile phase buffer B (0.1% TFA in 100% ACN) in a LC-MS/MS analysis. The separated peptides were analyzed online in a positive survey scan mode on a nano-ESI-Q-TOF instrument. Subsequently, the spectral data were processed with PLGS and MASCOT.

A series of the analysis processes afforded the final identification results given in FIG. 8. Of the analysis results, carbonic anhydrase 12 was identified in common from the antigens purified by both the 4B4 and the 27B6 monoclonal antibody, as expected, and was found to exist on cell surfaces. The other proteins cannot be antigens for the 4B4 and the 27B6 monoclonal antibody because they are intracellular proteins. Thus, they seemed to be impurities that were included due to imperfect separation and purification. Four peptides were separated by 27B6: QFLLTNNGHSVK (SEQ ID NO: 22), WTYFGPDGENSWSK (SEQ ID NO: 23), GQEAFVPGFNIEELLPER (SEQ ID NO: 24), and YKGQEAFVPGFNIEELLPER (SEQ ID NO: 25). Three peptides were separated by 4B4: QFLLTNNGHSVK (SEQ ID NO: 22), EMINNFR (SEQ ID NO: 26), and GVIYKPATK (SEQ ID NO: 27). Of them, the sequence QFLLTNNGHSVK was analyzed in common in both 4B4 and 27B6. FIG. 9 shows the amino acid sequence of carbonic anhydrase 12 precursor isoform 1, with the analyzed peptide sequence expressed in bold. FIG. 8 lists proteins identified by LC-MS/MS analysis from purified antigens. FIG. 9 shows the amino acid sequence of carbonic anhydrase 12 isoform 1, in which amino acid sequences of the antigens for 4B4 and 27B6 antibodies, detected by LC-MS/MS, are marked.

7-3: Assay of Antigen for 4B4 and 27B6 Monoclonal Antibodies (ELISA)

To evaluate the antigen identification results obtained by LC-MS/MS, the reactivity of the 4B4 and the 27B6 monoclonal antibody to the recombinant protein carbonic anhydrase 12 (R&D Systems) were examined by ELISA and Western blotting assay.

The recombinant protein CA12 was plated at a density of 100 ng/well into Maxisrop ELISA plates and incubated at 37° C. for 1 hr. To each of the antigen-coated wells, 200 μl of a 1× blocking buffer (Sigma) was added, followed by incubation at 37° C. for 1 hr for blocking. 4B4, 27B6, and an anti-CA12 monoclonal antibody (R&D Systems) were plated, together with 100 μl of PBS, into the plates. After incubation for 1 hr at 37° C., the plates were washed with PBS to remove unbound antibodies. Subsequently, a dilution of goat anti-mouse IgG-HRP (Jackson) was added to the wells, reacted for 30 min, and washed with PBS. Color development was accomplished for 10 min with 50 μl of TMB in each well, and stopped with 50 μl of sulfuric acid. Absorbance at 450 nm was read. Although the reactivity of the 27B6 monoclonal antibody to the recombinant carbonic anhydrase 12 was low, reactivity signals of 4B4, 27B6, and anti-CA12 monoclonal antibody (R&D Systems) against the recombinant antigen are shown in FIG. 10. FIG. 10 shows the identification of carbonic anhydrase 12 as an antigen for the 4B4 and the 27B6 monoclonal antibody, as analyzed by ELISA assay.

7-4: Assay of Antigen for 4B4 and 27B6 Monoclonal Antibodies (Western blotting)

Figure 11:
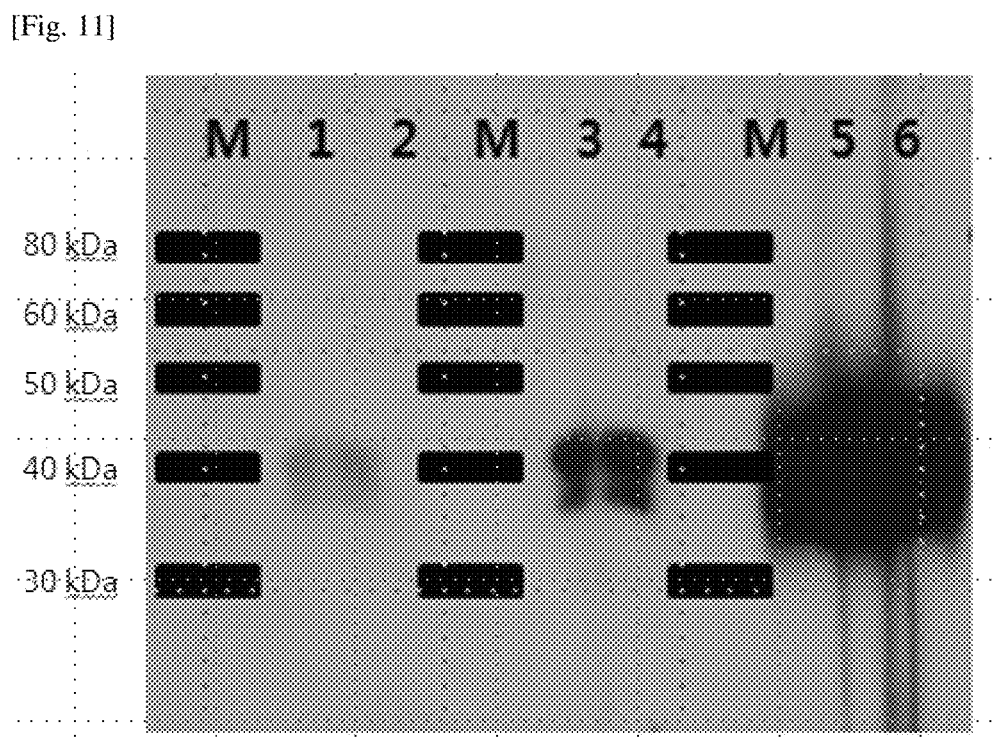

The recognition of carbonic anhydrase 12 as an antigen by the 4B4 and the 27B6 monoclonal antibody, proven in the previous experiment, was confirmed by Western blotting. The recombinant carbonic anhydrase 12 was boiled for 3 min, loaded into an 8% separating sodium dodecyl sulfate-polyacrylamide gel, and run by electrophoresis. The separated proteins were transferred to a nitrocellulose membrane which was then blocked with 5% skim milk (Sigma) and treated with the 4B4, 27B6, or anti-CA12 monoclonal antibody (R&D Systems) (27B6: lanes 1 and 2, 4B4: lanes 3 and 4, anti-CA12 monoclonal antibody: lanes 5 and 6). After three rounds of washing with a wash buffer (0.1% Tween-20 in PBS), the antibody was coupled with peroxidase-conjugated goat anti-mouse IgG (Sigma, Saint Louis, USA). After the nitrocellulose membrane was washed with a wash buffer, bands were visualized using an enhanced chemiluminescence detection system (ECL, Amersham, Sweden). The results are shown in FIG. 11. FIG. 11 shows the identification of carbonic anhydrase 12 as an antigen for the 4B4 and the 27B6 monoclonal antibody, as analyzed by Western blotting assay. The recombinant CA12 was read at 40 kDa by all of the 4B4, 27B6, and anti-CA12 monoclonal antibodies (R&D Systems).

7-5: Assay of Antigen for 4B4 and 27B6 Monoclonal Antibodies (Sandwich ELISA)

ELISA and WB assays demonstrated that 4B4 and 27B6 monoclonal antibodies recognize carbonic anhydrase 12 as an antigen, but the detection signal of the 27B6 monoclonal antibody was relatively low. To compensate for the relatively low signal, Sandwich ELISA was conducted as follows. The chimeric 4B4 or 27B6 monoclonal antibody was plated at a concentration of 100 ng/well into Maxisrop ELISA plates and incubated at 37° C. for 1 hr. To each of the antigen-coated wells, 200 μl of 1× blocking buffer (Sigma) was added, followed by incubation at 37° C. for 1 hr for blocking. Two-fold serial dilutions of the recombinant carbonic anhydrase 12 staring from 100 ng/ml were added to wells, incubated at 37° C. for 1 hr, and washed with PBS to remove unbound antigens. Subsequently, the 4B4 monoclonal antibody and the 27B6 monoclonal antibody were added at a concentration of 100 ng/well to chimeric 27B6-coated wells and chimeric 4B4-coated wells, respectively. Following 1 hr of incubation at 37° C., the wells were washed with PBS to remove unbound antibodies. In addition, the bound antibodies were incubated with a dilution of goat anti-Mouse IgG-HRP (Jackson) for 30 min and washed with PBS. Color development was accomplished for 10 min with 50 μl of TMB in each well and stopped with 50 μl of sulfuric acid. The absorbance at 450 nm was read. When chimeric 27B6 and 4B4 were used as a capture antibody and a detector antibody, respectively, high reaction signals were read, as shown in FIG. 2. Both of the 4B4 and 27B6 monoclonal antibodies were therefore proven to recognize carbonic anhydrase 12 as an antigen.

FIG. 12 shows the concurrent recognition of carbonic anhydrase 12 by the 27B6 and 4B4 monoclonal antibodies, as measured by sandwich ELISA assay using the 27B6 and 4B4 monoclonal antibodies as capture/detector antibodies.

EXAMPLE 8

Epitope Mapping

To analyze an epitope, as shown in FIG. 13, recombinant antibodies, with or without the epitope determined in Example 8, were constructed, and analyzed for immune reactions.

8-1: Construction of CA12 Mutant Recombinant Gene

The recombinant vector pSec-Tag-CA 12 full-hFc was digested with BamHI and HindIII to prepare CA12 mutant recombinant genes. A recombinant gene in which a full base sequence of CA12 antigen was fused to hFc was inserted into pSec-Tag which was then allowed to express a recombinant fusion protein containing the full length of CA12 plus hFc. As seen in FIG. 13, deletion mutant-hFc constructs having various lengths within a range from the N terminus to amino acid 300 were prepared.

8-2: Expression of CA12 Mutant Recombinant Genes

Respective pSec-Tag vectors carrying the CA12 full-hFc and five different deletion mutant-hFc constructs were introduced into CHO cells with the aid of ViaFect (Promega).

Briefly, one day before transfection, CHO cells were plated and incubated. After the medium was exchanged with a fresh one, a complex of the vector and ViaFect was applied to the CHO cells and incubated for 48 hrs. Two days after transfection, the culture supernatant was collected and analyzed for the expression of the gene by detecting human Fc (hFc) through sandwich ELISA.

8-3: Assay of Epitope of Monoclonal Antibody

In order to examine a CA12 epitope recognized by the monoclonal antibodies of the present disclosure, 50 ng of an anti-human Ig antibody (Jackson Laboratory) was added to each well and incubated at 37° C. for 1 hr. The antibody fixed to the well, which would serve as a capture antibody, was blocked via incubation with 200 μl of a 1× blocking buffer (Sigma) at 37° C. for 1 hr in each well. Each of the respective cultures containing the CA12 full-hFc and the five different deletion mutant-hFc constructs was added at a concentration of 100 μl/well to the plates. Following 1 hr of incubation at 37° C., the wells were washed with PBS to remove unbound antibodies. Subsequently, a dilution of anti-mouse Ig, Fc specific-HRP (Jackson Laboratory) was added to the wells, reacted for 30 min, and washed with PBS. Color development was accomplished for 10 min with 50 μl of TMB in each well, and stopped with 50 μl of sulfuric acid. The absorbance at 450 nm was read. The presence of CA12 mutant-hFc proteins in the culture supernatants was examined using Capture & Detect Sandwich ELISA, with an anti-human Ig antibody serving as a control. The results are given in FIG. 13.

As can be seen in FIG. 13, the epitopes were located in a site from a.a. 25 to a.a. 57, which is a non-catalytic domain. Hence, the antibodies of the present disclosure do not bind to the catalytic domain of CA-XII, so they do not inhibit the enzymatic activity of CA-XII.

In detail, the epitope specific for the 27B6 antibody was found to have the amino acid sequence APVNGSKWTYFGPD of SEQ ID NO: 2 (the span from a.a. 25 to a.a. 38 on SEQ ID NO: 5), as analyzed by the deletion method. A three-dimensional crystal structure of CA-12 confined the epitope into 7 consecutive amino acids WTYFGPD (SEQ ID NO: 1) on the amino acid sequence of SEQ ID NO: 2. Further, the epitope specific for the 4B4 antibody was found to have the amino acid sequence GENSWSKKYPSCGGLLQSP of SEQ ID NO: 4 (the span from a.a. 39 to a.a. 57 on SEQ ID NO: 5) while a three-dimensional crystal structure of CA-12 confined the epitope into 14 consecutive amino acid sequence GENSWSKKYPSCGG of SEQ ID NO: 3 on the amino acid sequence of SEQ ID NO: 4.

EXAMPLE 9

Therapeutic Effect of Antibody on Solid Tumor (CDC)

9-1: CDC Effect in Lung Adenocarcinomic Cell Line

The lung adenocarcinomic cell line A549 cells were plated at a density of $5\times10^3$ cells/well into 96-well plates and cultured for 20-24 hrs in a 37° C., $CO_2$ incubator. After removal of the culture medium from each well, an RPMI medium, free of fetal bovine serum, was mixed with 10% human serum and the chimeric 27B6 antibody was added at a final concentration of 10 μg/ml to a mixture. This solution was plated at a concentration of 100 μl/well into the plates. The 4B4 antibody was also treated in the same manner. Following 3 hrs of incubation in a 37° C. $CO_2$ incubator, Ez-CyTox agent (DOGEN, KOREA) was added in an amount of 10 μl to each well. Incubation for 3.5 hrs in a 37° C., $CO_2$ incubator was followed by measuring absorbance at 450 nm on a plate reader. The results are given in FIG. 14. FIG. 14 shows the complement-dependent cytotoxic effects of the 27B6 antibody.

As can be seen in FIG. 14, the 27B6 and 4B4 monoclonal antibodies of the present disclosure exhibit complement-dependent cytotoxicity.

9-2: CDC Effect in Triple-Negative Breast Cancer

As a target cell, the lung adenocarcinomic cell line A549 was plated at a density of $1\times10^4$ cells/well into 96-well plates and cultured for 20-24 hrs in a 37° C., $CO_2$ incubator. After removal of the culture medium from each well, an RPMI medium free of fetal bovine serum was mixed with 10% human serum, and the antibody was added at a final concentration of 10 μg/ml to a mixture. This solution was plated at a concentration of 100 μl/well into the plates. The 4B4 antibody was also treated in the same manner. Following 3 hrs of incubation in a 37° C. $CO_2$ incubator, an Ez-CyTox viability kit (Daeil Lab, Seoul, Korea) was added in an amount of 10 μl to each well. Incubation for 4 hrs in a 37° C., $CO_2$ incubator was followed by reading absorbance at 450 nm. As shown in FIG. 15, the 27B6 monoclonal antibody of the present disclosure exhibited complement-dependent cytotoxicity against lung adenocarcinomic tumors (FIG. 15).

EXAMPLE 10

Therapeutic Effect of Antibody in Solid Tumor (ADCC)

10-1: Assay for Antibody-Dependent Cell-Mediated Cytotoxicity (ADCC-LDH Assay)

In order to prepare effector cells, Ficoll was added to a human blood sample (blood:Ficoll=1:2), followed by centrifugation at 2000 rpm for 20 min to obtain PBMCs (Peripheral Blood Mononuclear Cells). The PBMCs were stored at 37° C. in a 5% PBS-supplemented RPMI medium. The antibody-dependent cell-mediated cytotoxicity assay was conducted in conjunction with an LDH assay or a Luciferase assay.

As targets, various solid tumor cell lines—HT29 (colorectal cancer), A549 (lung adenocarcinoma), NCI-H460 (lung adenocarcinoma), and MCF7 (breast cancer)—were each plated at a density of $1\times10^4$ cells/well into 96-well plates and cultured for 18-20 hrs in a 37° C., $CO_2$ incubator. After removal of the culture medium from each well, the chimeric antibody was added at a concentration of 0 μg/mL, 0.1 μg/mL, or 1 μg/mL to a culture medium supplemented with 5% FBS, and then plated at a concentration of 100 μl/well into the plates, followed by incubation for 30 min in a 37° C. $CO_2$ incubator. Thereafter, the effector cells prepared above were plated at a density of $5\times10^5$ cells/well (50 times as many as the target cells), and cultured for 24 hrs in a 37° C. $CO_2$ incubator. For a positive control, a lysis buffer was added before incubation at 37° C. for 24 hrs. Following 24 hrs of incubation, the cell culture was centrifuged at 2500 rpm for 5 min. The supernatant thus obtained was measured for LDH (lactate dehydrogenase) activity to calculate the cell lysis (Promega assay kit). As shown in FIG. 16, the 27B6 monoclonal antibody of the present disclosure exhibited antibody-dependent cell-mediated cytotoxicity in various solid tumors (FIG. 16). FIG. 16 shows the antibody-dependent cell-mediated cytotoxic effects of the 27B6 antibody.

10-2: Antibody-Dependent Cell-Mediated Cytotoxicity Assay in Triple-Negative Breast Cancer (ADCC-LDH Assay)

In addition, the 27B6 antibody was found to exhibit high antibody-dependent cell-mediated cytotoxicity in triple-negative breast cancer cell lines for which no therapeutic agents had yet been developed (FIG. 17). FIG. 17 shows the antibody-dependent cell-mediated cytotoxic effects of the 27B6 antibody on triple-negative breast cancer cell lines.

10-3: Antibody-Dependent Cell-Mediated Cytotoxicity Assay (ADCC-Luciferase Assay)

Effector cells were prepared in the same manner as in Example 9-2.

As target cells, the breast cancer cell lines MDAMB231 and SK-BR3 were each plated at a density of $1.25\times10^4$ cells/well into 96-well plates and cultured for 20-24 hrs in a 37° C. $CO_2$ incubator. After removal of the culture medium from each well, 25 μl of an RPMI medium containing 4% low IgG FBS was added to each well in which the cells were plated. 27B6 and 4B4 antibodies were 3-fold diluted in serial from 10 μg/ml to 1.2 ng/ml in an RPMI medium containing 4% low IgG FBS. The serial antibody dilutions were each added in an amount of 25 μl/well, and the plates were covered with respective lids and left on a clean bench. ADCC reporter cells (ADCC Reporter Bioassay, Promega) were harvested from the cell culture and suspended at a concentration of $3\times10^6$ cells/ml in an RPMI medium containing 4% low IgG PBS. To each well was added 25 μl of the suspension of ADCC reporter cells, followed by 24 hrs of incubation in a 37° C. $CO_2$ incubator. Before the plates were withdrawn, a frozen luciferase substrate was thawed in a water bath. The plates were removed from the clean bench and left at room temperature for 15 min. The luciferase substrate was added at a concentration of 75 μl/well to the plates and reacted for 30 min in a dark condition, followed by measuring luminescence with a luminometer.

As seen in FIG. 19, 27B6 and 4B4 antibodies, after being defucosylated by treatment with kifunensine, exerted greater antibody-dependent cell-mediated cytotoxicity on MDAMB231 and SK-BR-3 than did corresponding fucosylated ones. FIG. 19 shows the antibody-dependent cell-mediated cytotoxicity of defucosylated 4B4 and 27B6 chimeric antibodies.

EXAMPLE 11

Therapeutic Effect of Defucosylated Antibody in Solid Tumor (ADCC)

11-1: Assay for ADCC of Defucosylated Chimeric 27B6 Antibody—Colon, Lung, Breast Cancer Cells producing the 27B6 or the 4B4 chimeric antibody were incubated with 100 ng/ml kifunensine to induce the defucosylation of antibody proteins. With regard to ADCC effects, the defucosylated antibodies were compared to corresponding fucosylated antibodies.

Assay for ADCC of Kifunensine-treated, ADCC-Enhanced, Chimeric 27B6 Antibody—Colon, Lung, Breast As can be seen in FIG. 18, the antibodies defucosylated by kifunensine were increased in antibody-dependent cell-mediated cytotoxicity against various solid tumor cell lines. FIG. 18 shows the antibody-dependent cell-mediated cytotoxicity of the defucosylated 27B6 chimeric antibody.

11-2: Assay for ADCC of Defucosylated Chimeric 27B6 Antibody—Triple-Negative Breast Cancer Using a luciferase ADCC assay, antibody-dependent cell-mediated cytotoxicity against the triple-negative breast cancer cell line MDAMB231 and the HER2 receptor-positive breast cancer cell line SK-BR3 was analyzed. Antibodies, after being defucosylated by treatment with kifunensine, exerted greater antibody-dependent cell-mediated cytotoxicity on MDAMB231 and SK-BR-3 than did corresponding fucosylated ones. FIG. 19 shows the antibody-dependent cell-mediated cytotoxicity of defucosylated 4B4 and 27B6 chimeric antibodies, as measured by a luciferase assay.

EXAMPLE 12

Therapeutic Effect of 27B6 and 4B4 Antibodies in Mouse Models 12-1: Cell Line Establishment Animal models with human breast cancer were established using the triple-negative breast cancer cell lines MDA-MB-231 and MDA-MB-453. First, MDA-MB-231 or MDA-MB-453 was subcutaneously injected at a dose of $1.5\times10^8$ cells (in RPMI: Matrigel mixture) into the right flank of mice. The injected mice were randomly classified into test and control groups.

FIG. 20 further shows the binding of 27B6 and 4B4 antibodies to the surface of MDA-MB231 cells utilized in the animal experiment, and FIG. 21 shows the results of the animal experiment using the antibodies, demonstrating that the antibodies suppress the growth and size of MDA-MB231-induced tumor.

As test materials, the 27B6 fucosylated chimeric antibody, 27B6 defucosylated chimeric antibody, 4B4 fucosylated chimeric antibody, and 4B4 defucosylated chimeric antibody were inoculated into breast cancer cells. Three days later, the cells were intraperitoneally injected at a dose of 12 mg/kg to each mouse. Injection was conducted twice a week for three weeks. Tumor sizes were measured just before injection. The inhibitory activity of the anti-CA12 antibodies against breast cancer was expressed as the tumor volume calculated according to the following formula: (long axis$\times$ short axis$^2$)/2.

12-2: Inhibitory Activity of Anti CA12 Antibodies Against Triple-Negative Breast Cancer Targeting a CA12 epitope specifically expressed on triple-negative breast cancer, anti-CA12 antibodies (27B6, 4B4) were assayed for inhibitory activity against triple-negative breast cancer (FIGS. 22 and 23).

Breast tumors were decreased in volume by 27B6, and the fucosylated antibody was superior in inhibitory activity against tumor growth to the corresponding defucosylated antibody. The inhibitory activity of the 27B6 fucosylated antibody against the growth of breast cancer tumors was found in both MDA-MB-231 and MDA-MB-453. The antibodies inhibited tumor growth at a rate of 98% in the MDA-MB-453 model and at a rate of 55% in the MDA-MB-231 model (FIG. 22). FIG. 22 shows the inhibitory activity of 27B6 antibodies against triple-negative breast cancer.

In addition, 4B4 antibodies, whether fucosylated or defucosylated, were found to inhibit tumor growth. Further, 4B4 antibodies were superior to 27B6 antibodies with regard to inhibitory activity against tumor growth. Still higher inhibitory activity was detected in the defucosylated form than in the fucosylated form. Particularly, complete remission was observed in the MDA-MB-453 model as the tumor did not grow further after day 21 (FIG. 23). FIG. 23 shows the inhibitory activity of the 4B4 antibodies against triple-negative breast cancer.

EXAMPLE 13

Effect of Antibody on Cell Survival

When the antibodies were applied to CA12-positive cancer cells, the effects of the antibodies on cell growth and survival were examined. To this end, cells were plated at a density of $3\times10^4$ cells/well into 96-well flat bottom plates one day before application (10% RPMI). After 24 hrs, the RPMI was removed, and fresh 5% RPMI containing the antibody was added in an amount of 100 μl to each well.

After 24 hrs, a CytoTox 96® Non-Radioactive Cytotoxicity Assay kit (Promega, Cat. #G1780) was plated at a concentration of 50 μl/well and incubated for 30 min at room temperature. Cell viability was measured using a spectrophotometer. Twenty four hours after the antibody was applied to MDA-MB231 cells, the cell viability was measured.

The measurements are shown in FIG. 24. The administration of the antibodies neither promoted nor degraded cell viability. The antibodies did not inhibit CA12 enzymatic activity, and had no influences on tumor cell growth. Therefore, the antibodies according to the present disclosure were found to exhibit anti-tumor activity via ADCC and CDC through the immune system.

Cell viability was measured 24 hrs, 48 hrs and 72 hrs after the administration of the antibody to A549. No significant changes in cell viability were observed compared to the cells to which no antibodies were administered. FIGS. 24 and 25 show that the binding of the 4B4 antibody alone to tumor cells does not affect the growth of the tumor cells.

The 4B4 antibody, as an anti-CA12 antibody, had no influence on cell growth only when the antibody was bound to cells. This seems to be attributable to the fact that the 4B4 antibody does not affect the enzymatic activity of CA12 because it binds to an N-terminal non-enzymatic region of the CA12 antigen.

EXAMPLE 14

Combination of Antibody Therapy and Radiotherapy

An examination was made to see whether or not a combination of the antibody of the present disclosure and radiotherapy could bring about an increased anticancer effect.

Briefly, the 27B6 antibody of the present disclosure was used in combination with 5 μg/ml cisplatin, 2 Gy radiation, or 4 Gy radiation, and A549 cells were analyzed for CA12 expression via flow cytometry. As a result, both cisplatin and radiation were found to increase the expression of CA12 on cell surfaces, with the maximum expression level induced by 4 Gy radiation. This indicates that a combination of the anti-CA12 antibody of the present disclosure with radiotherapy is able to affect the growth of tumor cells (upper diagram in FIG. 26).

To assay the effect of the combined therapy on the growth of tumor cells, as shown in the lower diagram of FIG. 26, the viability of the cancer cell line A549 was measured via an MTT assay after it was treated with a combination of the 27B6 antibody and radiotherapy. In FIG. 26, the lower graph shows the effects of a combination of the 27B6 antibody and radiotherapy on cell viability. As can be seen in FIG. 26, a combination of 27B6 and radiotherapy induced cell death at higher rates, compared to the antibody alone or a combination of an isotype control antibody and radiotherapy.

What is claimed is:

1. An antibody or an antigen-binding fragment thereof, binding to carbonic anhydrase, wherein the antibody or an antigen-binding fragment thereof comprises a CDR-H1 comprising SEQ ID No: 6, a CDR-H2 comprising SEQ ID No: 7, a CDR-H3 comprising SEQ ID No: 8, a CDR-L1 comprising SEQ ID No: 9, a CDR-L2 comprising SEQ ID No: 10, and a CDR-L3 comprising SEQ ID No: 11.

2. The antibody or antigen-binding fragment thereof according to claim 1, wherein the antibody or antigen-binding fragment thereof binds to an epitope which is a peptide consisting of 7 to 93 consecutive amino acids containing the amino acid sequence of SEQ ID NO: 1 among amino acid sequence of SEQ ID NO: 5.

3. The antibody or antigen-binding fragment thereof according to claim 1, wherein the antibody or antigen-binding fragment thereof binds to an epitope which is a peptide consisting of 14 to 93 consecutive amino acids containing the amino acid sequence of SEQ ID NO: 2 among amino acid sequence of SEQ ID NO: 5.

4. The antibody or antigen-binding fragment thereof according to claim 3, wherein the antibody or antigen-binding fragment thereof binds to an epitope which is a peptide consisting of 7 to 14 consecutive amino acids containing the amino acid sequence of SEQ ID NO: 1 among amino acid sequence of SEQ ID NO: 2.

5. The antibody or antigen-binding fragment thereof according to claim 1, wherein the antibody or antigen-binding fragment thereof binds to an epitope which is a peptide consisting of 7 to 93 consecutive amino acids containing the amino acid sequence of SEQ ID NOs: 1, or 2.

6. The antibody or antigen-binding fragment thereof according to claim 1, wherein the antibody comprises amino acid sequences comprising amino acids of SEQ ID No: 12 of $V_H$ and amino acid sequences comprising amino acids of SEQ ID No: 13 of $V_L$.

7. The antibody or antigen-binding fragment thereof according to claim 1, wherein the antibody or the antigen-binding fragment thereof is coupled to labeling agents, toxins, or anti-tumor drugs.

8. The antibody or antigen-binding fragment thereof according to claim 7, wherein the labeling agent is selected from the group consisting of a radioisotope, a hapten or a fluorescent, a chromogen, and a dye.

9. The antibody or antigen-binding fragment thereof according to claim 7, wherein the toxin is selected from the group consisting of a radioisotope, a small molecule, a peptide, and a protein.

10. The antibody or antigen-binding fragment thereof according to claim 7, wherein the antibody or antigen-binding fragment thereof is coupled with a toxin to form a fusion protein.

11. A pharmaceutical composition, comprising the antibody or antigen-binding fragment thereof that binds to carbonic anhydrase according to claim 1.

12. The pharmaceutical composition according to claim 11, wherein the antibody or antigen-binding fragment thereof is coupled to a toxin.

13. The pharmaceutical composition according to claim 11, further comprising an anti-cancer agent.

14. A composition for detecting a solid cancer that comprises the antibody or antigen-binding fragment thereof according to claim 1, wherein the solid cancer is breast cancer, lung cancer, colorectal cancer, stomach cancer, prostate cancer, and liver cancer.

15. The composition for detecting a solid cancer according to claim 14, wherein the antibody or the antigen-binding fragment thereof is coupled to labeling agents.

* * * * *